United States Patent
DiRocco et al.

(10) Patent No.: US 10,597,422 B2
(45) Date of Patent: Mar. 24, 2020

(54) PROCESS FOR MAKING CHLORO-SUBSTITUTED NUCLEOSIDE PHOSPHORAMIDATE COMPOUNDS

(71) Applicant: Merck Sharp & Dohme Corp., Rahway, NJ (US)

(72) Inventors: Daniel DiRocco, Lebanon, NJ (US); Artis Klapars, Edison, NJ (US); Edward C. Sherer, Hillsborough, NJ (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 16/248,273

(22) Filed: Jan. 15, 2019

(65) Prior Publication Data

US 2019/0144485 A1     May 16, 2019

Related U.S. Application Data

(62) Division of application No. 15/427,674, filed on Feb. 8, 2017, now Pat. No. 10,214,554.

(60) Provisional application No. 62/407,668, filed on Oct. 13, 2016, provisional application No. 62/292,628, filed on Feb. 8, 2016.

(51) Int. Cl.

| | | |
|---|---|---|
| *C07D 239/00* | (2006.01) |
| *C07D 421/00* | (2006.01) |
| *C07D 517/00* | (2006.01) |
| *C07H 19/10* | (2006.01) |
| *C07H 19/06* | (2006.01) |
| *C07H 19/24* | (2006.01) |
| *C07D 487/04* | (2006.01) |
| *C07H 9/06* | (2006.01) |
| *C07H 1/00* | (2006.01) |
| *C07H 1/02* | (2006.01) |

(52) U.S. Cl.
CPC ........... *C07H 19/10* (2013.01); *C07D 487/04* (2013.01); *C07H 1/00* (2013.01); *C07H 1/02* (2013.01); *C07H 9/06* (2013.01); *C07H 19/06* (2013.01); *C07H 19/24* (2013.01)

(58) Field of Classification Search
None
See application file for complete search history.

(56) References Cited

FOREIGN PATENT DOCUMENTS

| | | |
|---|---|---|
| CN | 102329281 A | 1/2012 |
| WO | 2013/177219 A1 | 11/2013 |
| WO | WO2014058801 A1 | 4/2014 |
| WO | 2015139602 A1 | 9/2015 |

OTHER PUBLICATIONS

Awano, H., et al, "Nucleosides and Nucleotides, 128. (s'S)-2'-Deoxy-2-C-Methyl-5-Iodouridine (SMIU) as a Novel Potent Anti-Herpes Virus Agent", Bioorganic & Medicinal Chemistry Letters, 1994, pp. 367-370, vol. 4, No. 2.

Berge, S.M., et al.,, "Pharmaceutical Salts", J. Pharm. Sci, 1977, pp. 1-19, vol. 66, No. 1.

Gould, Salt Selections for Basic Drugs, Intl. J. Pharmaceutics, 1986, pp. 201-217, vol. 33.

Hayakawa, H., et al, "Reaction of Organometallic Reagents With 2'- and 3'-Ketouridine Derivtves: Synthesis of Uracil Nucleosides Branched at the 2'- and 3'-Positions", Chem Pharm. Bull., 1987, pp. 2605-2608, vol. 35.

Liu, S., et al, "First Catalytic Enantioselective Synthesis of P-stereogenic Phosphoramides Via Kinetic Resolution Promoted by a Chiral Bicyclic Imidazole Nucleophilic Catalyst", Tetrahedron: Asymmetry, 2012, pp. 329-332, vol. 23.

Reese, C.B., et al, "Acyl Migration in Ribonucleoside Derivatives", Tetrahedron Letters, 1965, pp. 2467-2472, vol. 29.

Zhang, Z., et al, "Chiral Bicycle Imidazole Nucleophilic Catalysts: Rational Design, Facile Synthesis, and Successful Application in Asymmetric Steglich Rearrangement", Journal American Chemical Society, 2010, pp. 15939-15941, vol. 132.

Zhang, Z., et al, "Chiral Bicyclic Imidazole Nucleophilic Catalysts: Design, Synthesis, and Application to the Kinetic Resolution of Arylalkylcarbinols", Adv. Synth. Catal., 2014, pp. 3164-3170, vol. 356.

*Primary Examiner* — Patrick T Lewis
(74) *Attorney, Agent, or Firm* — Jeffrey P. Bergman; Catherine D. Fitch

(57) ABSTRACT

The present invention is directed to a process for making Chloro-Substituted Nucleoside Phosphoramidate Compounds of formula (I):

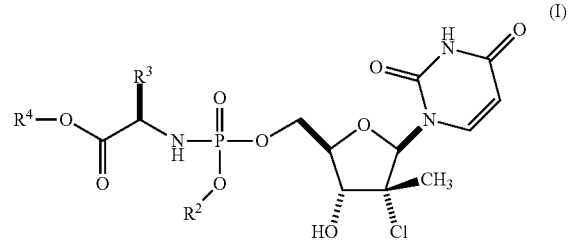

which are useful for the treatment and prophylaxis of HCV infection. The present invention is also directed to compounds that are useful as synthetic intermediates for making the compounds of formula (I).

2 Claims, No Drawings

PROCESS FOR MAKING CHLORO-SUBSTITUTED NUCLEOSIDE PHOSPHORAMIDATE COMPOUNDS

CROSS-REFERENCE TO RELATED APPLICATIONS

This application is a divisional of pending U.S. application Ser. No. 15/427,674, filed Feb. 8, 2017, which is claims priority to U.S. Provisional Application No. 62/292,628, filed Feb. 8, 2016, and U.S. Provisional Application No. 62/407,668, filed Oct. 13, 2016. Each of the aforementioned priority applications is incorporated by reference in its entirety.

FIELD OF THE INVENTION

The present invention is directed to a process for making Chloro-Substituted Nucleoside Phosphoramidate Compounds which are useful for the treatment or prophylaxis of HCV infection. The present invention is also directed to compounds that are useful as synthetic intermediates in the process of the invention.

BACKGROUND OF THE INVENTION

Hepatitis C virus (HCV) infection is a major health problem that leads to chronic liver disease, such as cirrhosis and hepatocellular carcinoma, in a substantial number of infected individuals, estimated to be 2-15% of the world's population. Once infected, about 20% of people clear the virus, but the rest harbor HCV the rest of their lives. Ten to twenty percent of chronically infected individuals eventually develop liver-destroying cirrhosis or cancer. HCV is transmitted parenterally by contaminated blood and blood products, contaminated needles, sexually or vertically from infected mothers or carrier mothers to their off-spring.

Inhibition of HCV NS5B polymerase prevents formation of the double-stranded HCV RNA and therefore constitutes an attractive approach to the development of HCV-specific antiviral therapies.

Various substituted nucleoside compounds are known inhibitors of the HCV NS5B protease enzyme. Included in these nucleosides are nucleoside phosphoramidate compounds which are useful in the treatment of infection by HCV and in the treatment, prophylaxis, or delay in the onset or progression of HCV infection. Representative nucleoside phosphoramidate compounds that are useful for treating HCV infection are described, for example, in International Patent Publication Nos. WO 2013/177219 and WO 2014/058801. Among the compounds disclosed in WO 2013/177219 is (R)-isopropyl 2-(((R)-(((2R,3R,4R,5R)-4-chloro-5-(2,4-dioxo-3,4-dihydropyrimidin-1(2H)-yl)-3-hydroxy-4-methyltetrahydrofuran-2-yl)methoxy)(phenoxy)phosphoryl)amino)propanoate, hereinafter referred to as Compound A. Compound A is a known inhibitor of HCV NS5B polymerase and is useful for the treatment of HCV infection. The structure of Compound A is as follows:

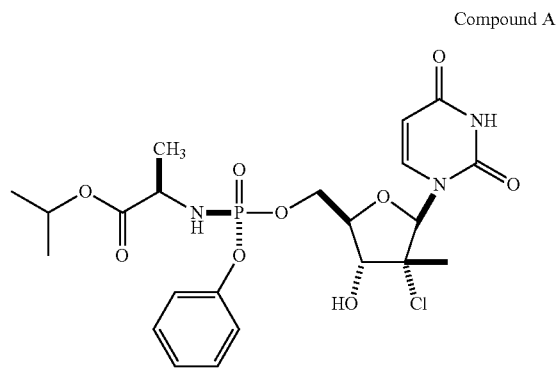 [SMILES: CC(C)OC(=O)[C@@H](C)N[P@@](=O)(OC[C@H]1O[C@@H](n2ccc(=O)[nH]c2=O)[C@](C)(Cl)[C@@H]1O)Oc1ccccc1]

Compound A

International Patent Publication Nos. WO 2013/177219 and WO 2014/058801 disclose methods that can be used to prepare Compound A and related nucleoside HCV NS5B inhibitors. These methods are practical routes for the preparation of Compound A and related nucleoside phosphoramidate compounds.

SUMMARY OF THE INVENTION

The present invention is directed to a process for making Chloro-Substituted Nucleoside Phosphoramidate Compounds of Formula (I) which are useful for the treatment and prophylaxis of HCV infection. More particularly, the present invention includes a method (alternatively referred to herein as "Process A") for preparing a compound of Formula (I):

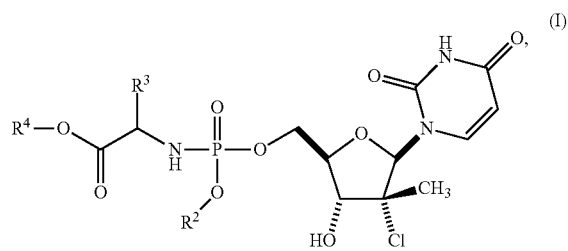

wherein said process comprising contacting a compound of formula (i):

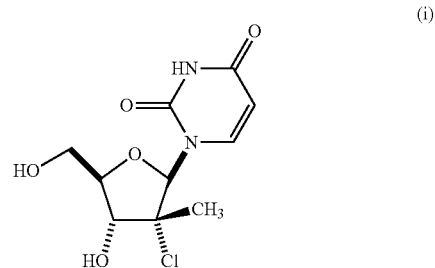 [SMILES: C[C@@]1(Cl)[C@H](O)[C@@H](CO)O[C@H]1n1ccc(=O)[nH]c1=O]

with a compound of formula (iia) or (iib):

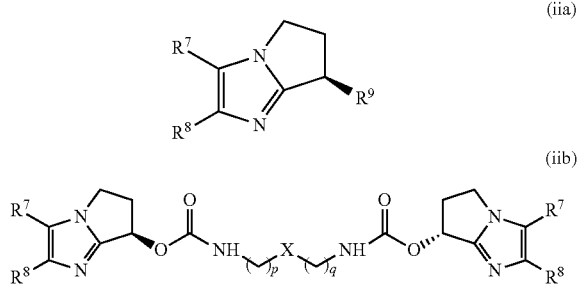

and a compound of formula (iii):

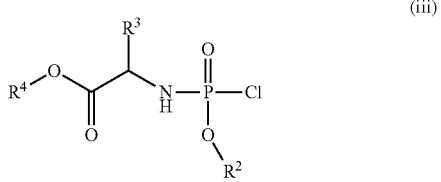

in the presence of a base, in an organic solvent A, at a temperature and for a time sufficient to form a compound of formula (I), wherein:

X is selected from $C_1$-$C_6$ alkylene, $C_6$-$C_{10}$ arylene, $C_4$-$C_{10}$ cycloalkylene, 5 or 6-membered monocyclic heteroarylene and 9 or 10-membered bicyclic heteroarylene, wherein said $C_6$-$C_{10}$ arylene group, said $C_4$-$C_{10}$ cycloalkylene group, said 5 or 6-membered monocyclic heteroarylene group and said 9 or 10-membered bicyclic heteroarylene group can be optionally substituted with one or more $R^5$ groups;

$R^2$ is selected from $C_6$-$C_{10}$ aryl, 5 or 6-membered monocyclic heteroaryl and 9 or 10-membered bicyclic heteroaryl, wherein said $C_6$-$C_{10}$ aryl group, said 5 or 6-membered monocyclic heteroaryl group and said 9 or 10-membered bicyclic heteroaryl group can be optionally substituted with one or more $R^5$ groups;

$R^3$ is selected from $C_1$-$C_6$ alkyl, $C_3$-$C_7$ cycloalkyl, phenyl and benzyl, wherein said $C_3$-$C_7$ cycloalkyl group, said phenyl group and the phenyl moiety of said benzyl group can be optionally substituted with one or more $R^5$ groups;

$R^4$ is selected from $C_1$-$C_6$ alkyl, $C_2$-$C_6$ alkenyl, —($C_1$-$C_3$ alkylene)$_m$-($C_3$-$C_7$ cycloalkyl) and —($C_1$-$C_3$ alkylene)$_m$-($C_6$-$C_{10}$ aryl);

each occurrence of $R^5$ is independently selected from —$C_1$-$C_6$ alkyl, halo, —$OR^6$, —$C(O)R^6$, —$CO_2R^6$, —$SR^6$, —$C_1$-$C_6$ hydroxyalkyl, —$C_1$-$C_6$ haloalkyl, —$N(R^6)_2$, —$S(O)R^6$, —$S(O)_2R^6$, —CN and —$NO_2$;

each occurrence of $R^6$ is independently selected from H, $C_1$-$C_6$ alkyl, $C_1$-$C_6$ haloalkyl, $C_1$-$C_6$ hydroxyalkyl, —($C_1$-$C_3$ alkylene)$_m$-($C_3$-$C_7$ cycloalkyl), —($C_1$-$C_3$ alkylene)$_m$-($C_6$-$C_{10}$ aryl), —($C_1$-$C_3$ alkylene)$_m$-(4 to 7-membered heterocycloalkyl), —($C_1$-$C_3$ alkylene)$_m$-(5- or 6-membered monocyclic heteroaryl) and —($C_1$-$C_3$ alkylene)$_m$-(9- or 10-membered bicyclic heteroaryl);

each occurrence of $R^7$ is independently selected from H, $C_1$-$C_6$ alkyl, phenyl, $C_3$-$C_7$ cycloalkyl, 4 to 7-membered monocyclic heterocycloalkyl and 5- or 6-membered monocyclic heteroaryl;

each occurrence of $R^8$ is independently selected from H, $C_1$-$C_6$ alkyl, phenyl, $C_3$-$C_7$ cycloalkyl, 4 to 7-membered monocyclic heterocycloalkyl and 5- or 6-membered monocyclic heteroaryl;

$R^9$ is selected from H, $C_1$-$C_6$ alkyl, phenyl, benzyl, —$OR^{10}$, —$OC(O)N(R^{11})_2$, $C_3$-$C_7$ cycloalkyl, 4 to 7-membered monocyclic heterocycloalkyl and 5- or 6-membered monocyclic heteroaryl;

$R^{10}$ is selected from $C_1$-$C_6$ alkyl, phenyl, benzyl and —$Si(R^{12})_3$;

each occurrence of $R^{11}$ is independently selected from H, $C_1$-$C_6$ alkyl, $C_3$-$C_{10}$ cycloalkyl and phenyl;

each occurrence of $R^{12}$ is independently selected from $C_1$-$C_6$ alkyl and phenyl;

each occurrence of m is independently 0 or 1;

p is 2, 3, 4 or 5; and q is 2, 3, 4 or 5, and wherein organic solvent A is selected from methyl ethyl ketone, acetone, dichloroethane, dimethyl ether, diethyl ether, methyl isobutyl ketone, toluene, THF, DCM, MTBE, DMF, propylene carbonate, 1,3-dioxolane, DME, 1,3-dimethyl-3,4,5,6-tetrahydro-2(1H)-pyrimidinone, 2-methyltetrahydrofuran, xylenes, ethyl acetate, NMP, anisole, isopropyl acetate, acetonitrile and mixtures thereof.

In another aspect, the present invention provides synthetic intermediates useful in the processes of the present invention.

Other embodiments, aspects and features of the present invention are either further described in or will be apparent from the ensuing description, examples, and appended claims.

DETAILED DESCRIPTION OF THE INVENTION

The present invention is directed to a process for making Chloro-Substituted Nucleoside Phosphoramidate Compounds of Formula (I) which are useful for inhibiting HCV NS5B polymerase, inhibiting the replication of HCV and for the treatment or prophylaxis of HCV infection.

Definitions and Abbreviations

The term "alkyl" as used herein, refers to an aliphatic hydrocarbon group, having from 1 to 20 carbon atoms wherein one of its hydrogen atoms is replaced with a bond. An alkyl group may be straight or branched. In one embodiment, an alkyl group has from 1-6 carbon atoms ("$C_1$-$C_6$ alkyl"). In another embodiment, an alkyl group has from 1-4 carbon atoms ("$C_1$-$C_4$alkyl"). Non-limiting examples of $C_1$-$C_6$ alkyl groups include methyl, ethyl, n-propyl, isopropyl, n-butyl, sec-butyl, isobutyl, tert-butyl, n-pentyl, neopentyl, isopentyl, n-hexyl, isohexyl and neohexyl. Non-limiting examples of $C_1$-$C_4$ alkyl groups include methyl, ethyl, n-propyl, isopropyl, n-butyl, sec-butyl, isobutyl and tert-butyl. An alkyl group may be unsubstituted or substituted by one or more substituents which may be the same or different, each substituent being independently selected from the group consisting of halo, alkenyl, alkynyl, aryl, cycloalkyl, cyano, hydroxy, —O-alkyl, —O-aryl, -alkylene-O-alkyl, alkylthio, —$NH_2$, —NH(alkyl), —N(alkyl)$_2$, —NH(cycloalkyl), —O—C(O)-alkyl, —O—C(O)-aryl, —O—C(O)-cycloalkyl, —C(O)OH and —C(O)O-alkyl. In one embodiment, an alkyl group is linear. In another embodiment, an alkyl group is branched. Unless otherwise indicated, an alkyl group is unsubstituted.

The term "alkylene," as used herein, refers to an alkyl group, as defined above, wherein one of the alkyl group's hydrogen atoms has been replaced with a bond. Non-limiting examples of alkylene groups include —$CH_2$—, —$CH_2CH_2$—, —$CH_2CH_2CH_2$—, —$CH_2CH_2CH_2CH_2$—, —CH(CH₃)CH₂CH₂—, —CH(CH₃)— and —CH₂CH(CH₃)CH₂—. In one embodiment, an alkylene group has from 1 to about 6 carbon atoms. In another embodiment, an alkylene group has from about 3 to about 5 carbon atoms. In another embodiment, an alkylene group is branched. In another embodiment, an alkylene group is linear. In one embodiment, an alkylene group is —CH₂—. The term "C₁-C₆ alkylene" refers to an alkylene group having from 1 to 6 carbon atoms.

The term "alkenyl," as used herein, refers to an aliphatic hydrocarbon group containing at least one carbon-carbon double bond and having one of its hydrogen atoms replaced with a bond. An alkenyl group may be straight or branched and contain from about 2 to about 15 carbon atoms. In one embodiment, an alkenyl group contains from about 2 to about 12 carbon atoms. In another embodiment, an alkenyl group contains from about 2 to about 6 carbon atoms ("C₂-C₆ alkenyl"). Non-limiting examples of alkenyl groups include ethenyl, propenyl, n-butenyl, 3-methylbut-2-enyl, n-pentenyl, octenyl and decenyl. An alkenyl group may be unsubstituted or substituted by one or more substituents which may be the same or different, each substituent being independently selected from the group consisting of halo, alkenyl, alkynyl, aryl, cycloalkyl, cyano, hydroxy, —O-alkyl, —O-aryl, -alkylene-O-alkyl, alkylthio, —NH₂, —NH(alkyl), —N(alkyl)₂, —NH(cycloalkyl), —O—C(O)-alkyl, —O—C(O)-aryl, —O—C(O)-cycloalkyl, —C(O)OH and —C(O)O-alkyl. The term "C₂-C₆ alkenyl" refers to an alkenyl group having from 2 to 6 carbon atoms. Unless otherwise indicated, an alkenyl group is unsubstituted.

The term "alkynyl," as used herein, refers to an aliphatic hydrocarbon group containing at least one carbon-carbon triple bond and having one of its hydrogen atoms replaced with a bond. An alkynyl group may be straight or branched and contain from about 2 to about 15 carbon atoms. In one embodiment, an alkynyl group contains from about 2 to about 12 carbon atoms. In another embodiment, an alkynyl group contains from about 2 to about 6 carbon atoms. Non-limiting examples of alkynyl groups include ethynyl, propynyl, 2-butynyl and 3-methylbutynyl. An alkynyl group may be unsubstituted or substituted by one or more substituents which may be the same or different, each substituent being independently selected from the group consisting of halo, alkenyl, alkynyl, aryl, cycloalkyl, cyano, hydroxy, —O-alkyl, —O-aryl, -alkylene-O-alkyl, alkylthio, —NH₂, —NH(alkyl), —N(alkyl)₂, —NH(cycloalkyl), —O—C(O)— alkyl, —O—C(O)-aryl, —O—C(O)-cycloalkyl, —C(O)OH and —C(O)O-alkyl. The term "C₂-C₆ alkynyl" refers to an alkynyl group having from 2 to 6 carbon atoms. Unless otherwise indicated, an alkynyl group is unsubstituted.

The term "C₁-C₆ hydroxyalkyl" as used herein, refers to C₁-C₆ alkyl group, as defined above, wherein one of the C₁-C₆ alkyl group's hydrogen atoms is replaced with a —OH group. A C₁-C₆ hydroxyalkyl group may be straight or branched and contain. Non-limiting examples of C₁-C₆ hydroxyalkyl groups include methanol, ethanol, isopropanol, and tert-butanol.

The term "C₆-C₁₀ aryl" refers to phenyl and naphthyl. In one embodiment, an aryl group is phenyl. A C₆-C₁₀ aryl group can be optionally substituted with one or more "ring system substituents" which may be the same or different, and are as defined herein below. In one embodiment, a C₆-C₁₀ aryl group is unsubstituted.

The term "3 to 7-membered cycloalkyl" refers to a non-aromatic mono- or ring system comprising from about 3 to about 7 ring carbon atoms. Examples of "3 to 7-membered cycloalkyls include cyclopropyl, cyclobutyl, cyclopentyl, cyclohexyl and cycloheptyl. A 3 to 7-membered cycloalkyl group can be optionally substituted with one or more "ring system substituents" which may be the same or different, and are as defined herein below. In one embodiment, a 3 to 7-membered cycloalkyl group is unsubstituted. A ring carbon atom of a 3 to 7-membered cycloalkyl may be functionalized as a carbonyl group. An illustrative example of such a 3 to 7-membered cycloalkyl (also referred to herein as a "cycloalkanoyl" group) includes, but is not limited to, cyclobutanoyl:

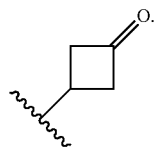 [SMILES: *C1CC(=O)C1]

The term "cycloalkylene," as used herein, refers to a cycloalkyl group, as defined above, wherein one of the cycloalkyl group's hydrogen atoms has been replaced with a bond. Non-limiting examples of cycloalkylene groups include. The term "C₃-C₇ cycloalkylene" refers to a cycloalkylene group having from 3 to 7 ring carbon atoms.

The term "halo" or "halogen" as used herein, refers to fluorine, chlorine, bromine and iodine (alternatively referred to as fluoro, chloro, bromo, and iodo).

The term "5 or 6-membered monocyclic heteroaryl," as used herein, refers to an aromatic monocyclic ring system comprising about 5 to about 6 ring atoms, wherein from 1 to 4 of the ring atoms is independently O, N or S and the remaining ring atoms are carbon atoms. A 5 or 6-membered monocyclic heteroaryl group can be optionally substituted by one or more "ring system substituents" which may be the same or different, and are as defined herein below. A 5 or 6-membered monocyclic heteroaryl group is joined via a ring carbon atom, and any nitrogen atom of a heteroaryl can be optionally oxidized to the corresponding N-oxide. The term "5 or 6-membered monocyclic heteroaryl" also encompasses a 5 or 6-membered monocyclic heteroaryl group, as defined above, which is fused to a benzene ring. Non-limiting examples of 5 or 6-membered monocyclic heteroaryls include pyridyl, pyrazinyl, furanyl, thienyl, pyrimidinyl, pyridone (including N-substituted pyridones), isoxazolyl, isothiazolyl, oxazolyl, oxadiazolyl, thiazolyl, pyrazolyl, furazanyl, pyrrolyl, triazolyl, 1,2,4-thiadiazolyl, pyrazinyl, pyridazinyl, benzofurazanyl, indolyl, azaindolyl, benzimidazolyl, benzothienyl, imidazolyl, benzimidazolyl, thienopyridyl, thienopyrimidyl, pyrrolopyridyl, imidazopyridyl, isoquinolinyl, 1,2,4-triazinyl, benzothiazolyl and the like, and all isomeric forms thereof. Unless otherwise indicated, a 5 or 6-membered monocyclic heteroaryl group is unsubstituted.

The term "5 or 6-membered monocyclic heteroarylene," as used herein, refers to a bivalent group derived from a 5 or 6-membered monocyclic heteroaryl group, as defined above, by removal of a hydrogen atom from a ring carbon of a 5 or 6-membered monocyclic heteroaryl group. In one embodiment, a 5 or 6-membered monocyclic heteroarylene group contains 5 ring atoms. In another embodiment, a 5 or 6-membered monocyclic heteroarylene group contains 6 ring atoms. A 5 or 6-membered monocyclic heteroarylene group is divalent and either available bond on a 5 or 6-membered monocyclic heteroarylene group can connect to either group flanking the 5 or 6-membered monocyclic heteroarylene group. For example, the group "A-5 or 6-membered monocyclic heteroarylene-B," wherein the 5 or 6-membered monocyclic heteroarylene group is:

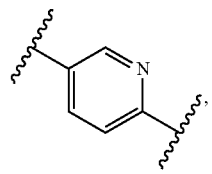 [SMILES: *c1ccc(*)nc1]

is understood to represent both:

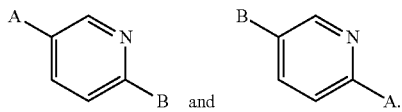

The term "9 or 10-membered bicyclic heteroaryl," as used herein, refers to an aromatic bicyclic ring system comprising about 9 to about 10 ring atoms, wherein from 1 to 4 of the ring atoms is independently O, N or S and the remaining ring atoms are carbon atoms. A 9 or 10-membered bicyclic heteroaryl group can be optionally substituted by one or more "ring system substituents" which may be the same or different, and are as defined herein below. A 9 or 10-membered bicyclic heteroaryl group is joined via a ring carbon atom, and any nitrogen atom of a heteroaryl can be optionally oxidized to the corresponding N-oxide. Non-limiting examples of 9 or 10-membered bicyclic heteroaryls include quinoxalinyl, phthalazinyl, oxindolyl, imidazo[1,2-a]pyridinyl, imidazo[2,1-b]thiazolyl, benzofurazanyl, indolyl, azaindolyl, benzimidazolyl, benzothienyl, quinolinyl, benzimidazolyl, quinazolinyl, pyrrolopyridyl, imidazopyridyl, isoquinolinyl, benzoazaindolyl and the like, and all isomeric forms thereof. Unless otherwise indicated, a 9 or 10-membered bicyclic heteroaryl group is unsubstituted.

The term "9 or 10-membered bicyclic heteroarylene," as used herein, refers to a bivalent group derived from a 5 or 6-membered monocyclic heteroaryl group, as defined above, by removal of a hydrogen atom from a ring carbon of a 9 or 10-membered bicyclic heteroarylene group. In one embodiment, a 9 or 10-membered bicyclic heteroarylene group contains 5 ring atoms. In another embodiment, a 9 or 10-membered bicyclic heteroarylene group contains 6 ring atoms. A 9 or 10-membered bicyclic heteroarylene group is divalent and either available bond on a 9 or 10-membered bicyclic heteroarylene group can connect to either group flanking the 9 or 10-membered bicyclic heteroarylene group. For example, the group "A-9 or 10-membered bicyclic heteroarylene-B," wherein the 9 or 10-membered bicyclic heteroarylene group is:

is understood to represent both:

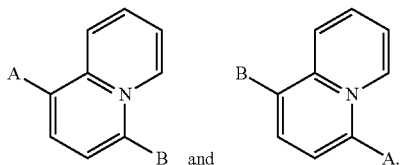

The term "heterocycloalkyl," as used herein, refers to a non-aromatic saturated monocyclic or multicyclic ring system comprising 3 to about 11 ring atoms, wherein from 1 to 4 of the ring atoms are independently O, S, N or Si, and the remainder of the ring atoms are carbon atoms. A heterocycloalkyl group can be joined via a ring carbon, ring silicon atom or ring nitrogen atom. In one embodiment, a heterocycloalkyl group is monocyclic and has from about 3 to about 7 ring atoms. In another embodiment, a heterocycloalkyl group is monocyclic has from about 4 to about 7 ring atoms. In another embodiment, a heterocycloalkyl group is bicyclic and has from about 7 to about 11 ring atoms. In still another embodiment, a heterocycloalkyl group is monocyclic and has 5 or 6 ring atoms. In one embodiment, a heterocycloalkyl group is monocyclic. In another embodiment, a heterocycloalkyl group is bicyclic. There are no adjacent oxygen and/or sulfur atoms present in the ring system. Any —NH group in a heterocycloalkyl ring may exist protected such as, for example, as an —N(BOC), —N(Cbz), —N(Tos) group and the like; such protected heterocycloalkyl groups are considered part of this invention. The term "heterocycloalkyl" also encompasses a heterocycloalkyl group, as defined above, which is fused to an aryl (e.g., benzene) or heteroaryl ring. A heterocycloalkyl group can be optionally substituted by one or more "ring system substituents" which may be the same or different, and are as defined herein below. The nitrogen or sulfur atom of the heterocycloalkyl can be optionally oxidized to the corresponding N-oxide, S-oxide or S,S-dioxide. Non-limiting examples of monocyclic heterocycloalkyl rings include oxetanyl, piperidyl, pyrrolidinyl, piperazinyl, morpholinyl, thiomorpholinyl, thiazolidinyl, 1,4-dioxanyl, tetrahydrofuranyl, tetrahydrothiophenyl, delta-lactam, delta-lactone and the like, and all isomers thereof.

A ring carbon atom of a heterocycloalkyl group may be functionalized as a carbonyl group. An illustrative example of such a heterocycloalkyl group is:

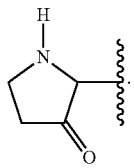 [SMILES: *C1NCCC1=O]

In one embodiment, a heterocycloalkyl group is a 5-membered monocyclic heterocycloalkyl. In another embodiment, a heterocycloalkyl group is a 6-membered monocyclic heterocycloalkyl. The term "3 to 6-membered monocyclic heterocycloalkyl" refers to a monocyclic heterocycloalkyl group having from 3 to 6 ring atoms. The term "4 to 7-membered monocyclic heterocycloalkyl" refers to a monocyclic heterocycloalkyl group having from 4 to 7 ring atoms. The term "7 to 11-membered bicyclic heterocycloalkyl" refers to a bicyclic heterocycloalkyl group having from 7 to 11 ring atoms. Unless otherwise indicated, a heterocycloalkyl group is unsubstituted.

The term "haloalkyl," as used herein, refers to an alkyl group as defined above, wherein one or more of the alkyl group's hydrogen atoms has been replaced with a halogen. In one embodiment, a haloalkyl group has from 1 to 6 carbon atoms. In another embodiment, a haloalkyl group is substituted with from 1 to 3 F atoms. Non-limiting examples of haloalkyl groups include —$CH_2F$, —$CHF_2$, —$CF_3$, —$CH_2Cl$ and —$CCl_3$. The term "$C_1$-$C_6$ haloalkyl" refers to a haloalkyl group having from 1 to 6 carbon atoms.

The term "hydroxyalkyl," as used herein, refers to an alkyl group as defined above, wherein one or more of the alkyl group's hydrogen atoms have been replaced with an —OH group. In one embodiment, a hydroxyalkyl group has from 1 to 6 carbon atoms. Non-limiting examples of hydroxyalkyl groups include —$CH_2OH$, —$CH_2CH_2OH$, —$CH_2CH_2CH_2OH$ and —$CH_2CH(OH)CH_3$. The term "$C_1$-$C_6$ hydroxyalkyl" refers to a hydroxyalkyl group having from 1 to 6 carbon atoms.

Unless expressly stated to the contrary in a particular context, any of the various cyclic rings and ring systems described herein may be attached to the rest of the compound of which they are a part at any ring atom (i.e., any carbon atom or any heteroatom) provided that a stable compound results.

Unless expressly stated to the contrary, all ranges cited above are inclusive; i.e., the range includes the values for the upper and lower limits of the range as well as all values in between.

When any variable occurs more than one time in a compound involved in the process of the invention (e.g., m, $R^5$ and $R^6$), its definition on each occurrence is independent of its definition at every other occurrence. Also, combinations of substituents and/or variables are permissible only if such combinations result in a stable compound.

Unless expressly stated to the contrary, substitution by a named substituent is permitted on any atom in a ring (e.g., cycloalkyl, aryl, or heteroaryl) provided such ring substitution is chemically allowed and results in a stable compound.

In reference to the compounds employed as reactants or reagents in the process of the invention (e.g., Compounds (i), (ii), (iii), etc. . . . ), a "stable" compound is one whose structure and properties remain or can be caused to remain essentially unchanged for a period of time sufficient to allow its use in the process of the invention so as to achieve the preparation of Compound of Formula (I). In reference to Compound of Formula (I), a "stable" compound is a compound which can be prepared in accordance with the process of the present invention and then isolated and whose structure and properties remain or can be caused to remain essentially unchanged for a period of time sufficient to allow use of the compound for its intended purpose; e.g., for the therapeutic administration to a subject who has HCV infection.

The term "salt(s)", as employed herein, denotes acidic salts formed with inorganic and/or organic acids, as well as basic salts formed with inorganic and/or organic bases. In addition, when a depicted compound contains both a basic moiety, such as, but not limited to a pyridine or imidazole, and an acidic moiety, such as, but not limited to a carboxylic acid, zwitterions ("inner salts") may be formed and are included within the term "salt(s)" as used herein. In one embodiment, the salt is a pharmaceutically acceptable (i.e., non-toxic, physiologically acceptable) salt. In another embodiment, the salt is other than a pharmaceutically acceptable salt. Salts of a compound, starting material or synthetic intermediate of the invention may be formed, for example, by reacting said compound, starting material or synthetic intermediate with an amount of acid or base, such as an equivalent amount, in a medium such as one in which the salt precipitates or in an aqueous medium followed by lyophilization.

Exemplary acid addition salts include acetates, ascorbates, benzoates, benzenesulfonates, bisulfates, borates, butyrates, citrates, camphorates, camphorsulfonates, fumarates, hydrochlorides, hydrobromides, hydroiodides, lactates, maleates, methanesulfonates, naphthalenesulfonates, nitrates, oxalates, phosphates, propionates, salicylates, succinates, sulfates, tartarates, thiocyanates, toluenesulfonates (also known as tosylates) and the like. Additionally, acids which are generally considered suitable for the formation of pharmaceutically useful salts from basic pharmaceutical compounds are discussed, for example, by P. Stahl et al, Camille G. (eds.) *Handbook of Pharmaceutical Salts. Properties, Selection and Use*. (2002) Zurich: Wiley-VCH; S. Berge et al, *Journal of Pharmaceutical Sciences* (1977) 66(1) 1-19; P. Gould, *International J. of Pharmaceutics* (1986) 33 201-217; Anderson et al, *The Practice of Medicinal Chemistry* (1996), Academic Press, New York; and in *The Orange Book* (Food & Drug Administration, Washington, D.C. on their website). These disclosures are incorporated herein by reference thereto.

Exemplary basic salts include ammonium salts, alkali metal salts such as sodium, lithium, and potassium salts, alkaline earth metal salts such as calcium and magnesium salts, salts with organic bases (for example, organic amines) such as dicyclohexylamine, t-butyl amine, choline, and salts with amino acids such as arginine, lysine and the like. Basic nitrogen-containing groups may be quarternized with agents such as lower alkyl halides (e.g., methyl, ethyl, and butyl chlorides, bromides and iodides), dialkyl sulfates (e.g., dimethyl, diethyl, and dibutyl sulfates), long chain halides (e.g., decyl, lauryl, and stearyl chlorides, bromides and iodides), aralkyl halides (e.g., benzyl and phenethyl bromides), and others.

Diastereomeric mixtures can be separated into their individual diastereomers on the basis of their physical chemical differences by methods well-known to those skilled in the art, such as, for example, by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereomers to the corresponding pure enantiomers. Sterochemically pure compounds may also be prepared by using chiral starting materials or by employing salt resolution techniques.

It is also possible that the compounds, starting materials and synthetic intermediates of the invention may exist in different tautomeric forms, and all such forms are embraced within the scope of the invention. For example, all keto-enol and imine-enamine forms of the compounds, starting materials and synthetic intermediates of the invention are included in the invention.

All stereoisomers (for example, geometric isomers, optical isomers and the like) of the present compounds, starting materials and synthetic intermediates of the invention (including those of the salts, solvates, hydrates and esters thereof), such as those which may exist due to asymmetric carbons on various substituents, including enantiomeric forms (which may exist even in the absence of asymmetric carbons), rotameric forms, atropisomers, and diastereomeric forms, are contemplated within the scope of this invention. If a compound, starting material or synthetic intermediate of the invention incorporates a double bond or a fused ring, both the cis- and trans-forms, as well as mixtures, are embraced within the scope of the invention.

The following abbreviations are used below and have the following meanings: AcOOH is acetic anhydride, BF$_3$.OEt is boron trifluoride etherate, n-Bu$_4$NBr is tetra n-butyl ammonium bromide, t-Bu is tertiary butyl, BSA is bis trimethylsilyl acetamide, CPME is DBU is 1,8-Diazabicyclo [5.4.0]undec-7-ene, DCM is dichloromethane, DMAC is dimethylacetamide, DMAP is N,N-dimethylaminopyridine, DME is 1,2-dimethoxyethane, DMF is N,N-dimethylformamide, DMI is 1,3-dimethyl-2-imidazolidinone, EDTA is ethylenediamine tetraacetic acid, Et$_2$O is diethyl ether, EtOAc is ethyl acetate, EtOH is ethanol, HPLC is high performance liquid chromatography, Hunig's Base is diisopropylethylamine, IPAc or IPAC is isopropyl acetate, i-PrOH is isopropanol, 2,6-lutidine is 2,6-dimethylpyridine, LC/MS is liquid chromatography/Mass Spectrometry, Me is methyl, MeCN is acetonitrile, MeMgBr is methyl magnesium bromide, MeOH is methanol, Me$_4$NF is tetramethylammonium fluoride, 2-MeTHF is 2-methyl tetrahydrofuran, MEK is methyl ethyl ketone, MIBK is methyl isobutyl ketone, MTBE is tert-butyl methyl ether, PhCH$_3$ is toluene, PhOCOCl is phenyl chloroformate, Ph$_3$SiH is triphenylsilane, pyr is pyridine, TBAF is tetrabutylammonium fluoride, TEMPO is (2,2,6,6-tetramethylpiperidin-1-yl)oxidanyl, TFAA is trifluoroacetic anhydride, THF is tetrahydrofuran, TLC is thin-layer chromatography, TMSCl is trimethylsilyl chloride, TMSCH$_2$MgBr is trimethylsilyl methylmagnesium bromide and TMSCH$_2$MgCl is trimethylsilyl methylmagnesium chloride.

The Processes of the Present Invention

The present invention is directed to a process for making Chloro-Substituted Nucleoside Phosphoramidate Compounds of Formula (I) which are useful for inhibiting the replication of HCV and for the treatment or prophylaxis of HCV infection. One aspect of the present invention is the process for making Compounds of Formula (I) as set forth above in the Summary of the Invention ("Process A").

In one embodiment, for Process A, the base used is a non-nucleophilic base.

In another embodiment, for Process A, the base used is an organic amine base.

In another embodiment, for Process A, the base used is 2,6-lutidine.

In one embodiment, for Process A, organic solvent A is dichloromethane, THF, 2-methyl THF, 1,3-dioxolane, methyl ethyl ketone or methyl isobutyl ketone.

In another embodiment, for Process A, organic solvent A is dichloromethane.

In another embodiment, for Process A, organic solvent A is THF.

In still embodiment, for Process A, organic solvent A is 2-methyl THF.

In another embodiment, for Process A, organic solvent A is 1,3-dioxolane.

In one embodiment, for Process A, the compound of formula (iia) is present and is:

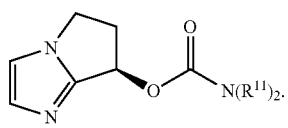

In another embodiment, for Process A, the compound of formula (iia) is present and is:

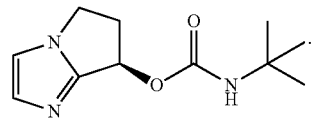 [SMILES: CC(C)(C)NC(=O)O[C@@H]1CCn2ccnc21]

In one embodiment, for Process A, the compound of formula (iib) is present.

In another embodiment, for Process A, the compound of formula (iib) is present and is selected from:

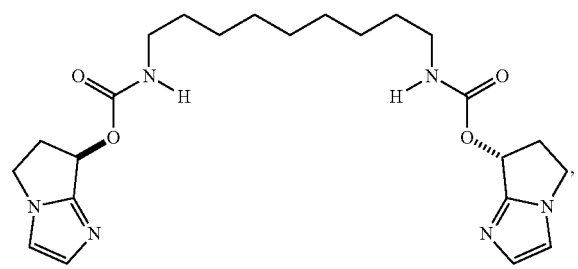

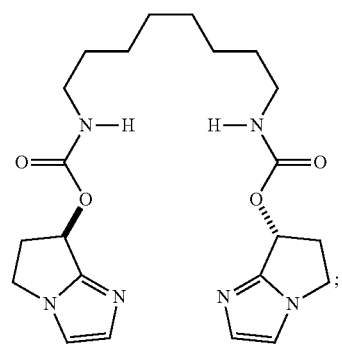

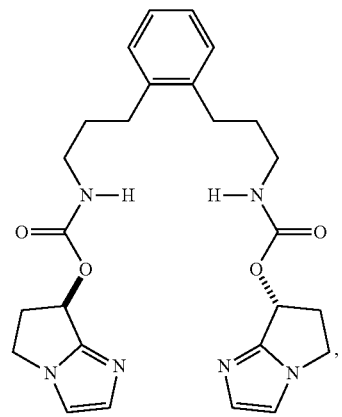

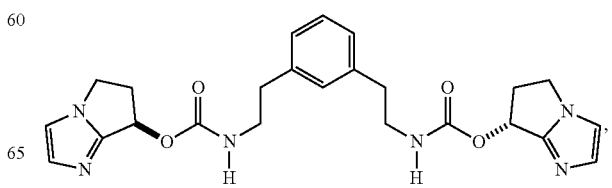

-continued

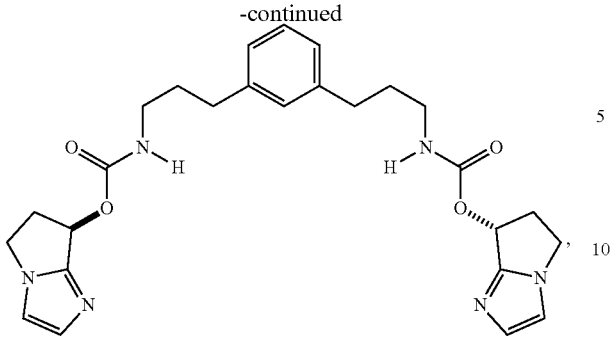

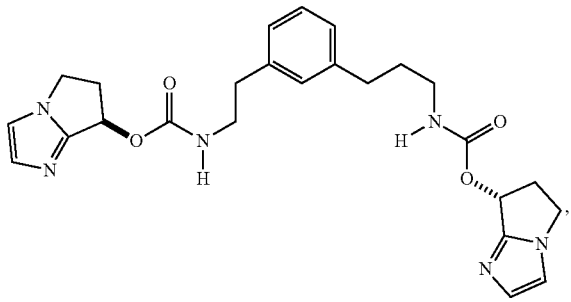

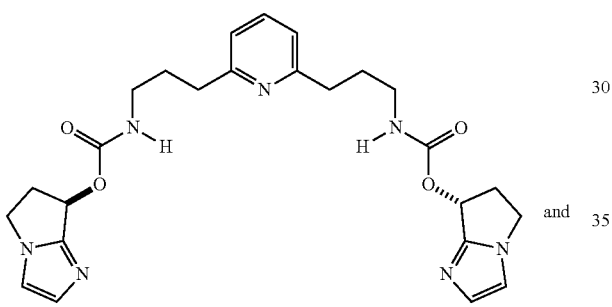

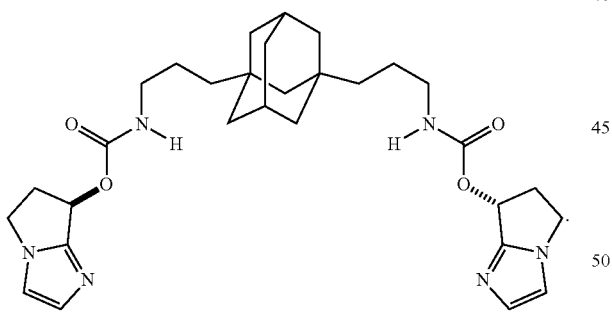

In one embodiment, for Process A:
the compound of formula (iia) is present and is:

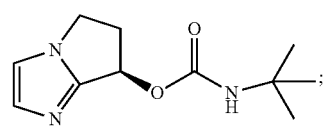 [SMILES: CC(C)(C)NC(=O)O[C@@H]1CCn2ccnc21]

the base is 2,6-lutidine; and
the solvent A is dichloromethane, methyl ethyl ketone or methyl isobutyl ketone;

the compound of formula (iii) is:

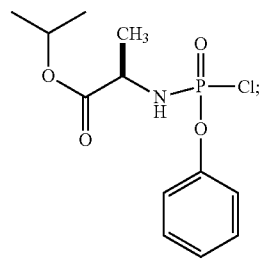 [SMILES: CC(C)OC(=O)[C@@H](C)NP(=O)(Cl)Oc1ccccc1]

and the organic solvent A is dichloromethane, methyl ethyl ketone or methyl isobutyl ketone.

In one embodiment, for Process A:
the compound of formula (iib) is:

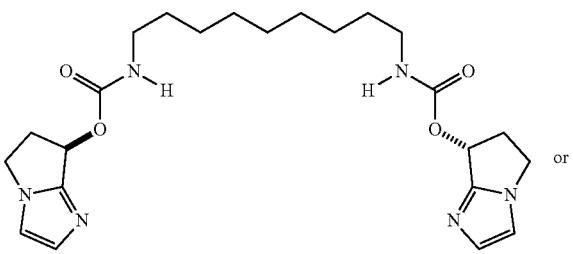

or

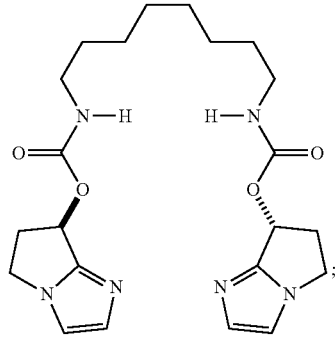

the base is 2,6-lutidine; and
the compound of formula (iii) is:

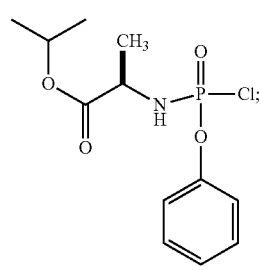 [SMILES: CC(C)OC(=O)[C@@H](C)NP(=O)(Cl)Oc1ccccc1]

and the organic solvent A is dichloromethane, methyl ethyl ketone or methyl isobutyl ketone.

In one embodiment, for Process A, the compound of Formula (I) has the formula (I'):

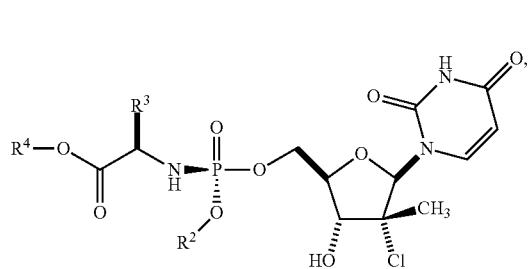

(I')

and the compound of formula (iii) has the formula (iii'):

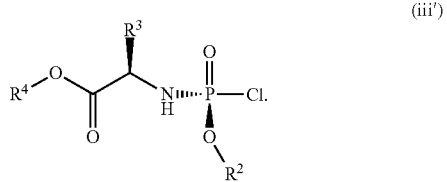

(iii')

In another embodiment, for Process A, the compound of Formula (I) has the formula (I"):

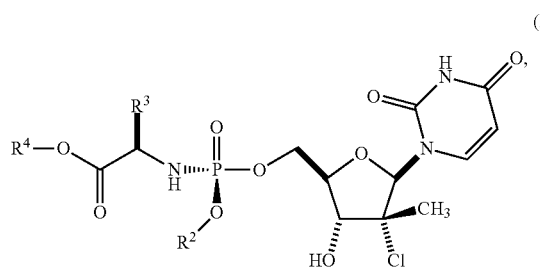

(I")

and the compound of formula (i) has the formula (iii"):

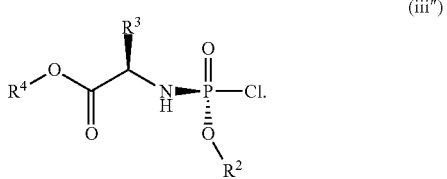

(iii")

In one embodiment, for Process A, the compound of formula (I) that is made by said process is:

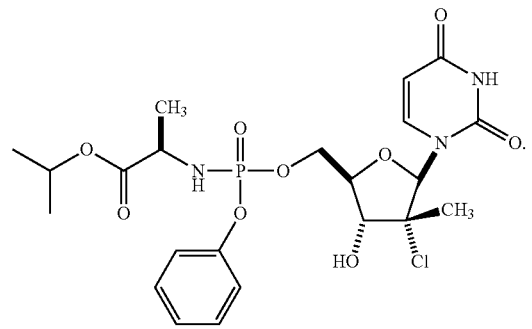 [SMILES: CC(C)OC(=O)[C@@H](C)NP(=O)(OC[C@H]1O[C@@H](n2ccc(=O)[nH]c2=O)[C@](C)(Cl)[C@@H]1O)Oc1ccccc1]

In another embodiment, for Process A, the compound of formula (I) that is made by said process is Compound A:

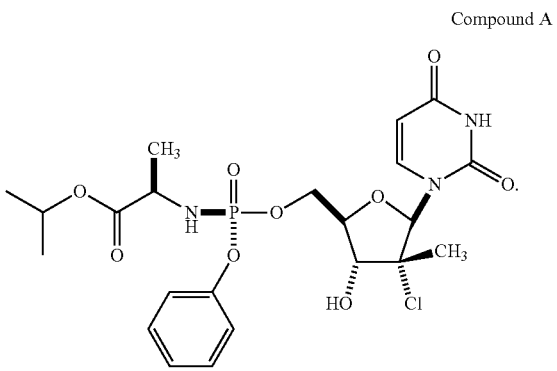 [SMILES: CC(C)OC(=O)[C@@H](C)N[P@@](=O)(OC[C@H]1O[C@@H](n2ccc(=O)[nH]c2=O)[C@](C)(Cl)[C@@H]1O)Oc1ccccc1]

Compound A

In another embodiment, for Process A, the compound of formula (I) that is made by said process is:

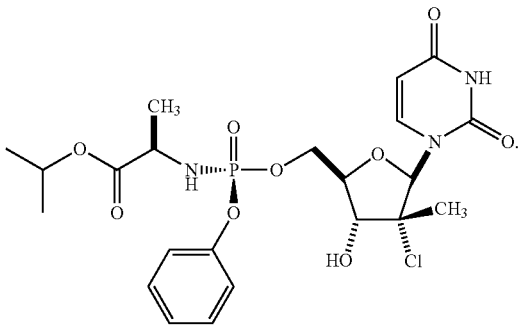 [SMILES: CC(C)OC(=O)[C@@H](C)N[P@](=O)(OC[C@H]1O[C@@H](n2ccc(=O)[nH]c2=O)[C@](C)(Cl)[C@@H]1O)Oc1ccccc1]

In one aspect, the present invention provides a process for making a compound of formula (i) ("Process B"):

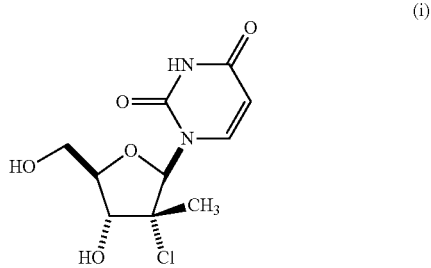 [SMILES: C[C@@]1(Cl)[C@H](O)[C@@H](CO)O[C@H]1n1ccc(=O)[nH]c1=O]

(i)

wherein said process comprises the steps:
(A) contacting a compound of Formula (B):

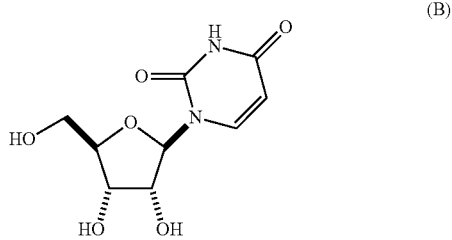 [SMILES: O=c1ccn([C@@H]2O[C@H](CO)[C@@H](O)[C@H]2O)c(=O)[nH]1]

(B)

with pivaloyl chloride, in the presence of a base in an optional organic solvent A, for a time and at a temperature sufficient to provide a mixture of a compound of Formula (C) and a compound of formula (D):

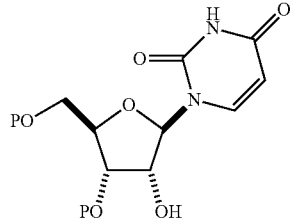

(C)

and

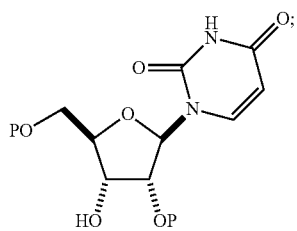

(D)

wherein P is pivaloyl and optional organic solvent A is selected from acetonitrile, toluene, dichloromethane, tetrahydrofuran, 2-methyltetrahydrofuran, ethyl acetate, isopropyl acetate, N,N-dimethylformamide, pyridine, N,N-dimethylacetamide and N-methylpyrrolidone, and mixtures thereof;

(B) contacting the mixture of the compound of formula (C) and the compound of formula (D) with an oxidizing agent in an organic solvent B, in the presence of an optional pH modifier, for a time and at a temperature sufficient to provide a compound of Formula (E):

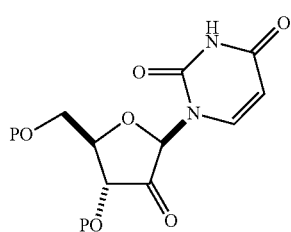

(E)

wherein P is pivaloyl and organic solvent B is selected from acetone, toluene, benzene, xylenes, cumene, cyclohexane, heptane, methylcyclohexane, dichloroethane, chlorobenzene, THF, anisole, ethyl acetate, isopropyl acetate, CPME, dichloromethane and mixtures thereof;

(C) contacting the compound of Formula (E) with a compound of formula $CH_3MgX$ in the presence of a salt of formula $R^{50}Cl_2$ or $(CH_3)_2AlX$ in an organic solvent C, for a time and at a temperature sufficient to provide a compound of Formula (F):

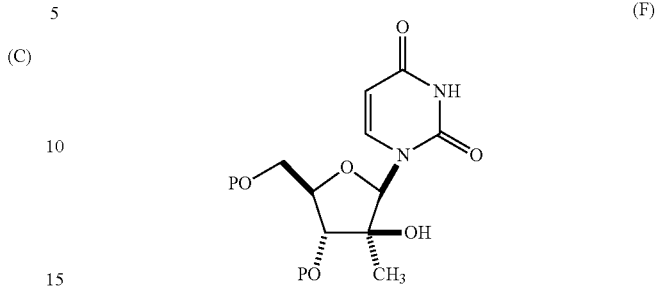

(F)

wherein P is pivaloyl; $R^{50}$ is Mn or Zn; X is Br, Cl or I; and organic solvent C is selected from THF, 2-methyl THF, diethyl ether, dibutylether, cyclopentyl methyl ether, toluene, dimethoxyethane, anisole, xylenes and mixtures thereof, (D) contacting the compound of Formula (F) with a dehydrating agent, in the presence or absence of catalytic TMSCl or catalytic HCl or elemental sulfur, in an organic solvent D for a time and at a temperature sufficient to form a compound of formula (G):

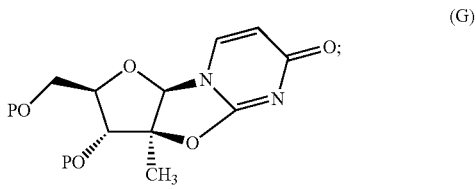

(G)

wherein P is a pivaloyl group and organic solvent D is selected from toluene, benzene, xylenes, cumene, cyclohexane, heptane, methylcyclohexane, dichloroethane, chlorobenzene, THF, anisole, ethyl acetate, isopropyl acetate, CPME and mixtures thereof;

(E) contacting the compound of formula (G) with a base in an organic solvent E for a time and at a temperature sufficient to provide a compound of Formula (A):

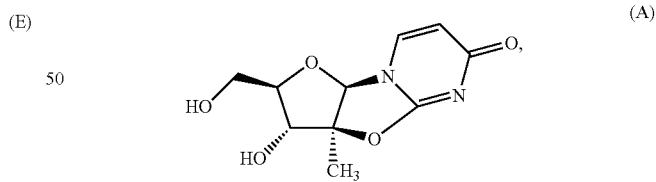

(A)

wherein organic solvent E is selected from organic alcohol solvents, toluene, benzene, xylenes, cumene, cyclohexane, heptane, methylcyclohexane, dichloroethane, chlorobenzene, DME, THF, anisole, ethyl acetate, isopropyl acetate, CPME, and mixtures thereof, and (F) contacting the compound of formula (A) with HCl or a compound of formula $R_{(4-n)}SiCl_n$ in an organic solvent E for a time and at a temperature sufficient to provide a compound of Formula (i), wherein R is $C_1$-$C_6$ alkyl or phenyl, and n is 1, 2 or 3.

In one embodiment, for Process B, Step (A), the base is an organic base.

In another embodiment, for Process B, Step (A), the base is pyridine.

In another embodiment, for Process B, Step (A), the optional organic solvent A is selected from acetonitrile, toluene, dichloromethane, tetrahydrofuran, pyridine and mixtures thereof.

In one embodiment, for Process B, Step (B), the oxidizing agent is (a) sodium hypochlorite/TEMPO in the presence of catalytic n-Bu$_4$NBr or (b) peracetic acid/TEMPO in the presence of catalytic n-Bu$_4$NBr.

In another embodiment, for Process B, Step (B), the optional pH modifier is absent.

In another embodiment, for Process B, Step (B), the optional pH modifier is present and is sodium borate.

In still another embodiment, for Process B, Step (B), the organic solvent B is toluene.

In one embodiment, for Process B, Step (C), the compound of formula CH$_3$MgX is CH$_3$MgBr.

In another embodiment, for Process B, Step (C), the salt of formula R$^{50}$Cl$_2$ is MnCl$_2$.

In another embodiment, for Process B, Step (C), the salt of formula R$^{50}$Cl$_2$ is ZnCl$_2$.

In still another embodiment, for Process B, Step (C), the salt of formula (CH$_3$)$_2$AlX is (CH$_3$)$_2$AlCl.

In another embodiment, for Process B, Step (C), the organic solvent C is 2-MeTHF, toluene or a mixture thereof.

In one embodiment, for Process B, Step (D), the dehydrating agent is selected from N,O-bis(trimethylsilyl)acetamide, trimethylsilylimidazole, bis(trimethylsilyl)urea, bis(trimethylsilyl)trifluoroacetamide, TMSCl and TMSOTf.

In another embodiment, for Process B, Step (D), the dehydrating agent is N,O-bis(trimethylsilyl)acetamide.

In another embodiment, for Process B, Step (D), elemental sulfur is present.

In still another embodiment, for Process B, Step (D), catalytic TMSCl is present.

In another embodiment, for Process B, Step (D), catalytic HCl is present.

In another embodiment, for Process B, Step (D), the organic solvent D is toluene.

In one embodiment, for Process B, Step (E), the base is selected from alkali metal carbonates, such as sodium carbonate, cesium carbonate and potassium carbonate; alkali metal alkoxides, such as lithium t-butoxide, sodium methoxide, sodium ethoxide, potassium methoxide and potassium ethoxide; organic amines, such as triethyl amine and Hunig's base; and DBU.

In another embodiment, for Process B, Step (E), the base is potassium carbonate.

In another embodiment, for Process B, Step (E), the base is DBU.

In still another embodiment, for Process B, Step (E), the organic solvent E is an organic alcohol solvent.

In another embodiment, for Process B, Step (E), the organic solvent E is a mixture of water and an organic alcohol solvent.

In another embodiment, for Process B, Step (E), the organic solvent E is methanol.

In one embodiment, for Process B, Step (F), the compound of formula (A) is contacted with HCl.

In another embodiment, for Process B, Step (F), the compound of formula (A) is contacted with TMSCl.

In another embodiment, for Process B, Step (F), the compound of formula (A) is contacted with Me$_2$SiCl$_2$.

In still another embodiment, for Process B, Step (F), the organic solvent E is DME, DMF or a mixture thereof.

In another embodiment, for Process B, Step (F), the oxidizing agent is (a) sodium hypochlorite/TEMPO in the presence of catalytic n-Bu$_4$NBr or (b) peracetic acid/TEMPO in the presence of catalytic n-Bu$_4$NBr.

In another embodiment, for Process B, Step (F), the compound of formula R$_{(4-n)}$SiCl$_n$ is Me$_3$SiCl or Me$_2$SiCl$_2$.

In one embodiment, for Process B:
for step (A):
 the base is pyridine; and
 the organic solvent A is pyridine;
and wherein for step (B):
 the oxidizing agent is (a) sodium hypochlorite/TEMPO in the presence of catalytic n-Bu$_4$NBr or (b) peracetic acid/TEMPO in the presence of catalytic n-Bu$_4$NBr; and
 the organic solvent B is toluene;
and wherein for step (C):
 the compound of formula CH$_3$MgX is CH$_3$MgBr;
 the compound of formula R$^{50}$Cl$_2$ is MnCl$_2$;
 the compound of formula (CH$_3$)$_2$AlX is (CH$_3$)$_2$AlCl; and
 the organic solvent C is toluene or anisole;
and wherein for step (D):
 the dehydrating agent is N,O-bis(trimethylsilyl)acetamide; and
 the organic solvent D is toluene or anisole;
and wherein for step (E):
 the base is DBU; and
 the organic solvent E is an organic alcohol;
and wherein for step (F):
 the compound of formula R$_{(4-n)}$SiCl$_n$ is (CH$_3$)$_3$SiCl or Me$_2$SiCl$_2$; and
 the organic solvent E is DME.

In one embodiment, for Process B, step (B) is replaced by the following steps (B') and (B"):
(B') contacting the mixture of the compound of formula (C) and the compound of formula (D) with BF$_3$.OEt in an organic solvent B for at least one hour; and
(B") contacting the solution resulting from step B' with an oxidizing agent, for a time and at a temperature sufficient to provide a compound of Formula (E):

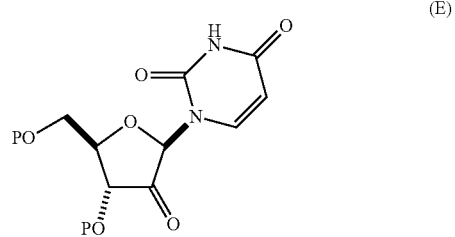

wherein P is pivaloyl and organic solvent B is selected from acetone, toluene, benzene, xylenes, cumene, cyclohexane, heptane, methylcyclohexane, dichloroethane, chlorobenzene, THF, ethyl acetate, isopropyl acetate, CPME, dichloromethane and mixtures thereof.

In another embodiment, for Process B, Step (B"), the oxidizing agent is (a) sodium hypochlorite/TEMPO in the presence of catalytic n-Bu$_4$NBr or (b) peracetic acid/TEMPO in the presence of catalytic n-Bu$_4$NBr.

In another embodiment, for Process B, step (D) is replaced by the following step D':
(D') contacting the compound of Formula (F) with a dehydrating agent, in the presence of a silylating agent and a photoredox catalyst, in the presence of visible light, in an organic solvent D' for a time and at a temperature sufficient to form a compound of formula (G):

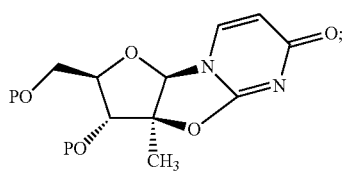

(G)

wherein P is a pivaloyl group and organic solvent D' is selected from toluene, benzene, xylenes, cumene, cyclohexane, heptane, methylcyclohexane, dichloroethane, chlorobenzene, THF, ethyl acetate, isopropyl acetate, eucalyptol, EtOAc, IPAC, CPME and mixtures thereof.

In one embodiment of Process B, for step (D'):

the dehydrating agent is N,O-bis(trimethylsilyl)acetamide;

the silylating agent is bis(trimethylsilyl)acetamide;

the photoredox catalyst is 9-mesityl-10-methylacridinium perchlorate;

the visible light is at a wavelength of about 450 nm; and the organic solvent D' is DME.

In one embodiment, for Process B, step (E) is replaced by the following step E':

(E') contacting the compound of Formula (A) with Me$_2$SiCl$_2$, in an organic solvent E' for a time and at a temperature sufficient to form a compound of formula (i). The organic solvent E' is DME.

In one aspect, the present invention provides a process for making a compound of formula (i') ("Process C"):

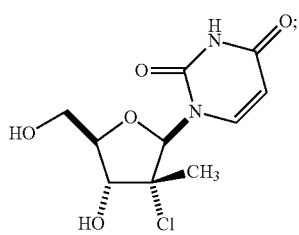

(i)

wherein said process comprises the steps:

(A) contacting a compound of Formula (B):

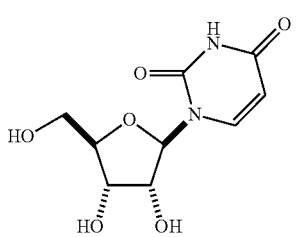

(B)

with pivaloyl chloride, in the presence of a base in an optional organic solvent A, for a time and at a temperature sufficient to provide a mixture of a compound of Formula (C) and a compound of formula (D):

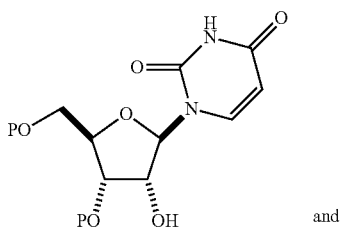

(C)

and

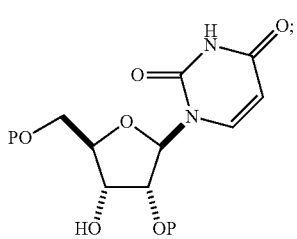

(D)

wherein P is pivaloyl and optional organic solvent A is selected from acetonitrile, toluene, dichloromethane, tetrahydrofuran, 2-methyltetrahydrofuran, ethyl acetate, isopropyl acetate, N,N-dimethylformamide, pyridine, N,N-dimethylacetamide and N-methylpyrrolidone, and mixtures thereof;

(B) contacting the mixture of the compound of formula (C) and the compound of formula (D) with an oxidizing agent and a bromide salt in an organic solvent B, for a time and at a temperature sufficient to provide a compound of Formula (E):

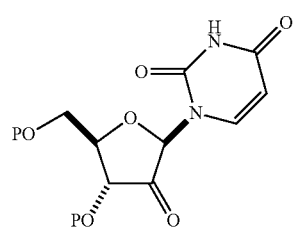

(E)

wherein P is pivaloyl and organic solvent B is selected from selected from acetone, toluene, benzene, xylenes, cumene, cyclohexane, heptane, methylcyclohexane, dichloroethane, chlorobenzene, THF, ethyl acetate, isopropyl acetate, CPME, dichloromethane and mixtures thereof;

(C) contacting the compound of Formula (E) with a compound of formula TMSCH$_2$MgX in an organic solvent C, for a time and at a temperature sufficient to provide a compound of Formula (H):

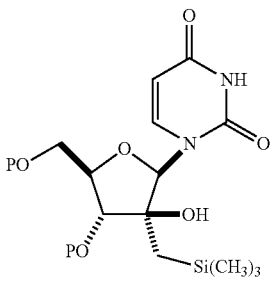

(H)

wherein P is pivaloyl; X is Br, Cl or I; and organic solvent C is selected from toluene, benzene, xylenes, cumene, cyclohexane, heptane, methylcyclohexane, dichloroethane, chlorobenzene, dichloromethane, THF, 2-methyl-THF, dimethoxyethane, ethylene glycol dimethyl ether, DME, anisole, CPME and mixtures thereof;

(D) (i) contacting the compound of Formula (H) with a fluoride ion in an organic solvent D; then (ii) contacting the product of step (i) with a base and an organic alcohol or water or a mixture thereof, for a time and at a temperature sufficient to provide a compound of Formula (J):

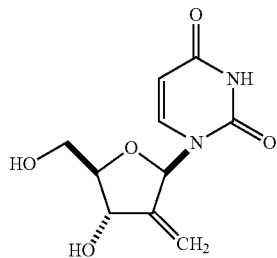

(J)

wherein solvent D is selected from toluene, acetonitrile, benzene, xylenes, cumene, chlorobenzene, THF, ethyl acetate, isopropyl acetate and CPME and mixtures thereof; and (E) contacting the compound of Formula (J) with FeCl$_3$ in the presence of a reducing agent in a solvent E, for a time and at a temperature sufficient to provide a compound of Formula (i), wherein solvent E is selected from water or an organic alcohol solvent, or a mixture thereof.

In one embodiment, for Process C, Step (A):
the base is pyridine; and
the organic solvent A is pyridine;
and wherein for step (B):
the oxidizing agent is (a) sodium hypochlorite/TEMPO in the presence of catalytic n-Bu$_4$NBr or (b) sodium hypochlorite/TEMPO in the presence of catalytic n-Bu$_4$NBr; and
the organic solvent B is toluene;
and wherein for step (C):
the compound of formula TMSCH$_2$MgX is TMSCH$_2$MgCl; and
the organic solvent C is toluene;
and wherein for step (D):
the fluoride ion source is a tetraalkyl ammonium fluoride or an alkali metal fluoride;
the base is an alkali metal carbonate or DBU; and
the organic alcohol is methanol;
and wherein for step (E):
the reducing agent is phenylsilane, tetramethyldisiloxane, diphenylsilane, triethylsilane or poly(methylhydrosiloxane); and
the solvent E is water, DME, an organic alcohol, tetramethyl disiloxane or a mixture thereof.

In one embodiment, for Process C, step (B) is replaced by the following steps (B') and (B"):

(B') contacting the mixture of the compound of formula (C) and the compound of formula (D) with BF$_3$.OEt in an organic solvent B for at least one hour; and (B") contacting the solution resulting from step B' with and oxidizing agent and peracetic acid, for a time and at a temperature sufficient to provide a compound of Formula (E):

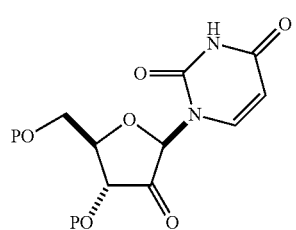

(E)

wherein P is pivaloyl and organic solvent B is selected from acetone, toluene, benzene, xylenes, cumene, cyclohexane, heptane, methylcyclohexane, dichloroethane, chlorobenzene, THF, ethyl acetate, isopropyl acetate, CPME, dichloromethane and mixtures thereof.

In another embodiment, for Process C, Step (B"), the oxidizing agent is (a) sodium hypochlorite/TEMPO in the presence of catalytic n-Bu$_4$NBr or (b) peracetic acid/TEMPO in the presence of catalytic n-Bu$_4$NBr.

In one embodiment, for Process C, Step D is replaced by the following step D':

(D') (i) contacting the compound of Formula (H) with an alcohol activating agent and a base in an organic solvent D', then (ii) contacting the product of step with a fluoride ion; and (i) for a time and at a temperature sufficient to provide a compound of Formula (J):

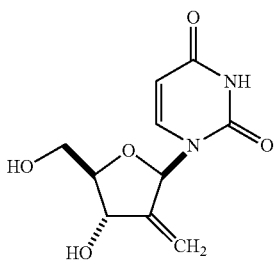

(J)

wherein solvent D' is selected from toluene, acetonitrile, benzene, xylenes, cumene, chlorobenzene, THF, 2-MeTHF, ethyl acetate, isopropyl acetate, acetonitrile, dimethoxyethane, N,N-dimethylformamide, N,N-dimethylacetamide, N-methylpyrrolidone and CPME and mixtures thereof.

In one embodiment, for Process C, step (D'):
the alcohol activating agent is an alkyl acid anhydride or an aryl acid anhydride;
the fluoride ion source is a tetraalkyl ammonium fluoride or an alkali metal fluoride; and
the base is N,N-dimethylaminopyridine; and
the organic solvent D' is acetonitrile.

In one embodiment, for Process C, Step D is replaced by the following step D":

(D") (i) contacting the compound of Formula (H) with a dehydrating agent, optionally in the presence of elemental sulfur, in an organic solvent D", then (ii) contacting the resulting product with a fluoride ion in an organic solvent D" for a time and at a temperature sufficient to form a compound of Formula (J):

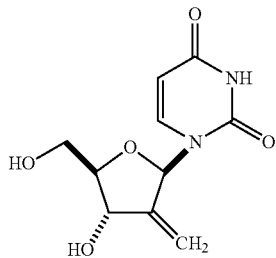

(J)

wherein solvent D" is selected from is selected from toluene, benzene, xylenes, cumene, dichloroethane, chlorobenzene, THF, ethyl acetate, acetonitrile, isopropyl acetate, CPME, dimethoxyethane, 2-MeTHF and mixtures thereof.

In one embodiment, for Process C, step (D"):

the dehydrating agent is N,O-bis-trimethylsilylacetamide;

the fluoride ion source is a tetraalkyl ammonium fluoride or an alkali metal fluoride; and the organic solvent D" is toluene or acetonitrile or a mixture thereof.

In one embodiment, for Process A, $R^2$ is $C_6$-$C_{10}$ aryl and $R^3$ and $R^4$ are each independently $C_1$-$C_6$ alkyl.

The Compounds of the Present Invention

The present invention is also directed to compounds that are useful as synthetic intermediates in the claimed processes for making the Chloro-Substituted Nucleoside Phosphoramidate Compounds of Formula (I). Accordingly, one aspect of the present invention is to provide novel compounds useful as synthetic intermediates for making the Compounds of Formula (I).

Compounds of the present invention include, but are not limited to the following compounds:

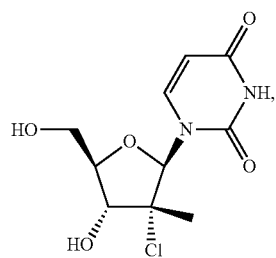

(i)

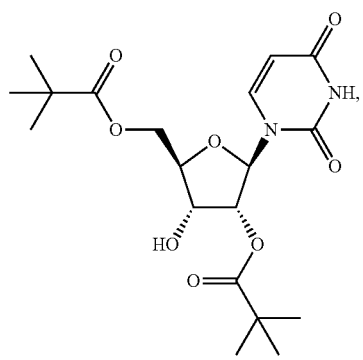

(1a)

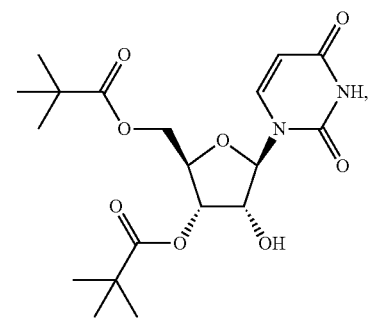

(1b)

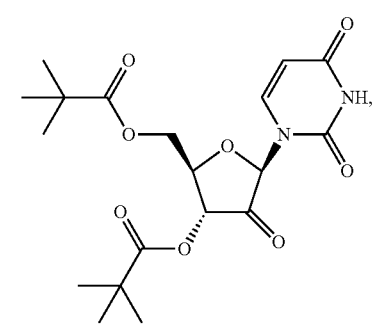

(2)

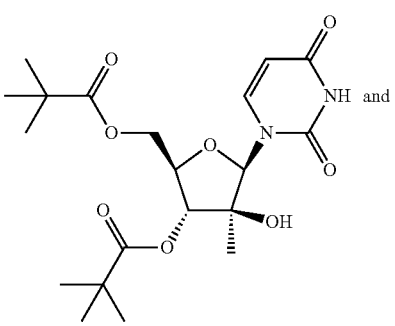

(3)

and

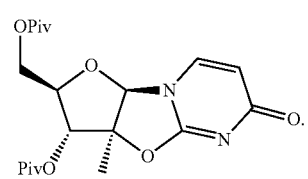

(4)

Additional compounds of the present invention include, but are not limited to the compounds of formula (iia'):

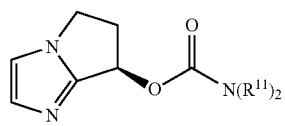

(iia')

wherein each occurrence of $R^{11}$ is independently selected from H, $C_1$-$C_6$ alkyl, $C_3$-$C_{10}$ cycloalkyl and phenyl.

Additional compounds of the present invention include, but are not limited to the compounds of formula (iib):

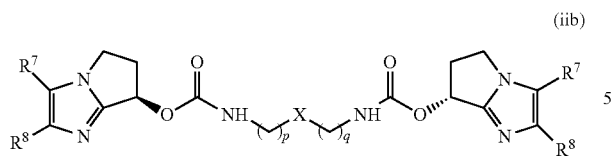

wherein

X is selected from $C_1$-$C_6$ alkylene, $C_6$-$C_{10}$ arylene, $C_4$-$C_{10}$ cycloalkylene, 5 or 6-membered monocyclic heteroarylene and 9 or 10-membered bicyclic heteroarylene, wherein said $C_6$-$C_{10}$ arylene group, said $C_4$-$C_{10}$ cycloalkylene group, said 5 or 6-membered monocyclic heteroarylene group and said 9 or 10-membered bicyclic heteroarylene group can be optionally substituted with one or more $R^5$ groups;

each occurrence of $R^5$ is independently selected from —$C_1$-$C_6$ alkyl, halo, —$OR^6$, —$C(O)R^6$, —$CO_2R^6$, —$SR^6$, —$C_1$-$C_6$ hydroxyalkyl, —$C_1$-$C_6$ haloalkyl, —$N(R^6)_2$, —$S(O)R^6$, —$S(O)_2R^6$, —CN and —$NO_2$;

each occurrence of $R^6$ is independently selected from H, $C_1$-$C_6$ alkyl, $C_1$-$C_6$ haloalkyl, $C_1$-$C_6$ hydroxyalkyl, —($C_1$-$C_3$ alkylene)$_m$-($C_3$-$C_7$ cycloalkyl), —($C_1$-$C_3$ alkylene)$_m$-($C_6$-$C_{10}$ aryl), —($C_1$-$C_3$ alkylene)$_m$-(4 to 7-membered heterocycloalkyl), —($C_1$-$C_3$ alkylene)$_m$-(5- or 6-membered monocyclic heteroaryl) and —($C_1$-$C_3$ alkylene)$_m$-(9- or 10-membered bicyclic heteroaryl);

each occurrence of $R^7$ is independently selected from H, $C_1$-$C_6$ alkyl, phenyl, $C_3$-$C_7$ cycloalkyl, 4 to 7-membered monocyclic heterocycloalkyl and 5- or 6-membered monocyclic heteroaryl;

each occurrence of $R^8$ is independently selected from H, $C_1$-$C_6$ alkyl, phenyl, $C_3$-$C_7$ cycloalkyl, 4 to 7-membered monocyclic heterocycloalkyl and 5- or 6-membered monocyclic heteroaryl;

each occurrence of m is independently 0 or 1;

p is 2, 3, 4 or 5; and q is 2, 3, 4 or 5.

Further compounds of the present invention include, but are not limited to the following compounds:

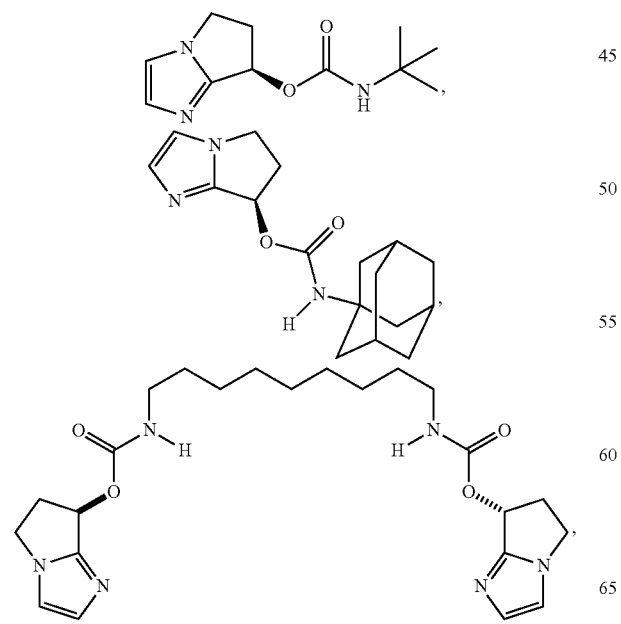

-continued

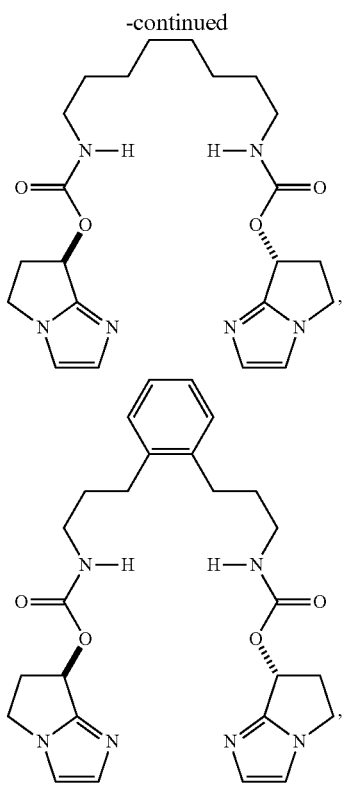

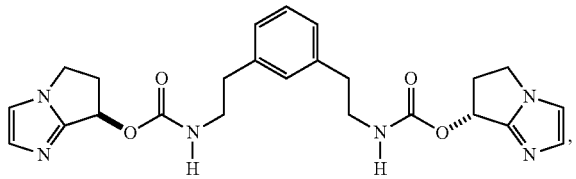

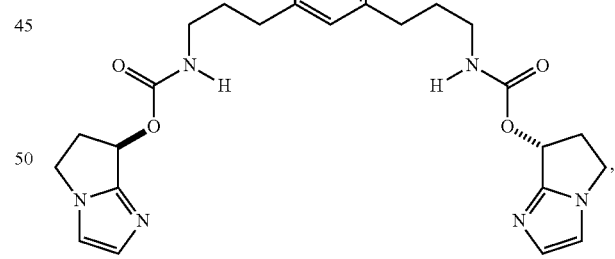

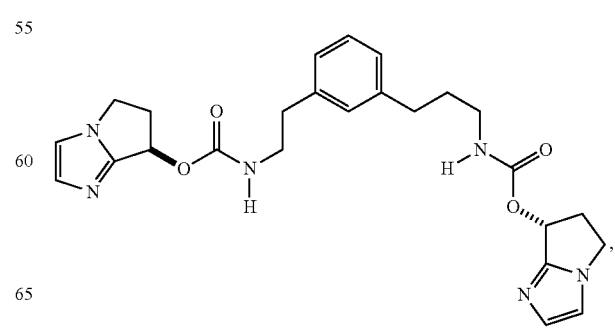

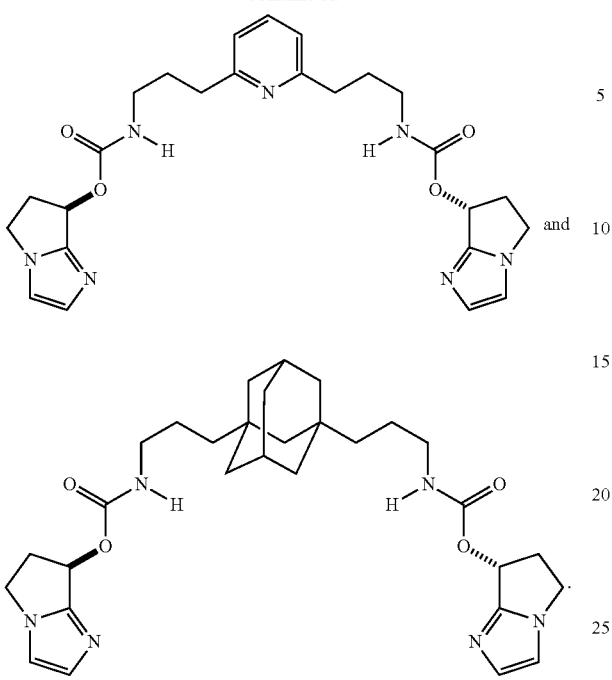

and

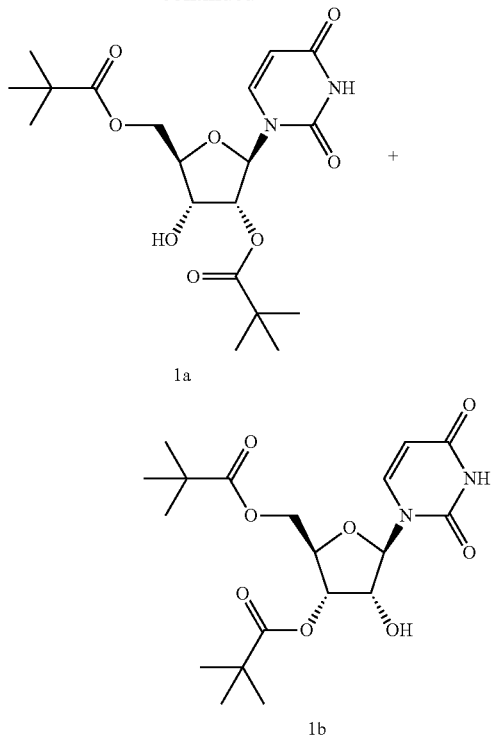

1a

1b

EXAMPLES

General Methods

Solvents, reagents, and intermediates that are commercially available were used as received. Reagents and intermediates that are not commercially available were prepared in the manner as described below. $^1$H NMR spectra were obtained on a Bruker Avance 500 (500 MHz) and are reported as ppm downfield from Me$_4$Si with number of protons, multiplicities, and coupling constants in Hertz indicated parenthetically. Where LC/MS data are presented, analyses was performed using an Applied Biosystems API-100 mass spectrometer and Shimadzu SCL-10A LC column: Altech platinum C18, 3 micron, 33 mm×7 mm ID; gradient flow: 0 minutes—10% CH$_3$CN, 5 minutes—95% CH$_3$CN, 5-7 minutes—95% CH$_3$CN, 7 minutes—stop.

The retention time and observed parent ion are given.

Example 1

Preparation of Compounds 1a and 1b

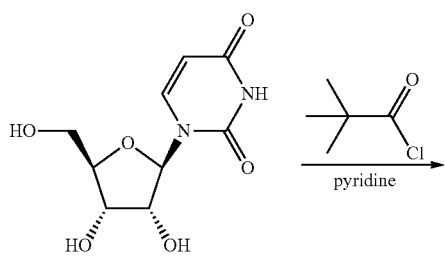

To a dry round bottom flask was charged uridine (10.0 g, 40.9 mmol) and anhydrous pyridine (50 mL) and the resulting mixture was cooled to 0° C. under N$_2$ atmosphere. To the mixture was slowly added pivaloyl chloride (10.6 mL, 86.0 mmol, 2.1 eq) while maintaining the internal temperature below 5° C. The reaction was then allowed to stir for about 15 hours at room temperature, after which time additional pivaloyl chloride (0.5 mL, 4.09 mmol) was added and the reaction was allowed to stir for an additional 15 hours at room temperature. To the reaction mixture was added water (40 mL) and the resulting solution was allowed to stir for about 15 hours at room temperature. The reaction mixture was then concentrated in vacuo and the resulting residue was taken up in toluene (100 mL) and washed sequentially with 2.5 N HCl (1×50 mL), 5% NaHCO$_3$ (1×50 mL) and saturated NaCl solution (1×50 mL). The collected organic phase was dried over MgSO$_4$, filtered and washed with toluene (2×50 mL) to provide a solution of compounds 1a and 1b (36:64 ratio of 1a:1b), which was used in the next step without further purification.

Compound 1a: $^1$H NMR (CDCl$_3$, 500 MHz): δ 9.99 (s, NH), 7.42 (d, J=8.1 Hz, 1H), 5.9 (d, J=3.7 Hz, 1H), 5.70 (d, J=8.2 Hz, 1H), 5.18 (dd, J=5.6, 3.8 Hz, 1H), 4.24-4.40 (m, 3H), 4.16 (dd, J=6.8, 4.2, 2.8 Hz, 1H), 3.71 (d, J=4.5 Hz, OH), 1.19 (s, 18H); $^{13}$C NMR (CDCl$_3$, 125 MHz,): δ 178.25, 177.97, 163.72, 150.21, 140.12, 102.74, 88.53, 81.60, 75.33, 69.09, 63.38, 38.92, 38.81, 27.17, 27.04; HRMS [M+H]$^+$ for C$_{19}$H$_{29}$N$_2$O$_8$ calc'd 413.1924; found 413.1928.

Compound 1b: $^1$H NMR (CDCl$_3$, 500 MHz): δ 10.25 (s, NH), 7.49 (d, J=8.2 Hz, 1H), 5.87 (d, J=4.8 Hz, 1H), 5.70 (d, J=8.2 Hz, 1H), 4.93 (t, J=5.2 Hz, 1H), 4.54 (d, J=4.8 Hz, OH), 4.24-4.40 (m, 4H), 1.17 (s, 18H); $^{13}$C NMR (CDCl$_3$, 125 MHz,): δ 177.94, 177.92, 163.62, 150.93, 139.29, 102.81, 89.83, 79.97, 73.51, 71.09, 63.07, 38.86, 38.81, 27.15, 27.00; HRMS [M+H]⁺ for $C_{19}H_{29}N_2O_8$ calc'd 413.1924; found 413.1917.

Example 2

Alternate Preparation of Compounds 1a and 1b

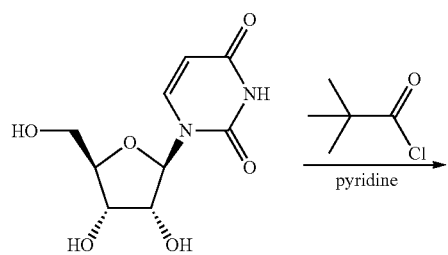

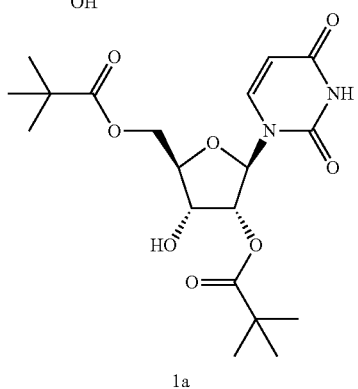

1a

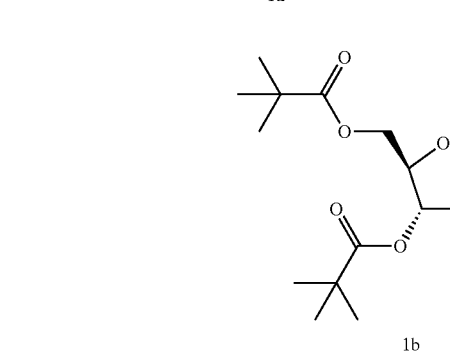

1b

To a dry round bottom flask was charged uridine (30.0 g, 123 mmol) and anhydrous pyridine (90 mL). The resulting mixture was cooled to 0° C. under a nitrogen atmosphere. To the mixture was slowly added pivaloyl chloride (32.6 g, 270 mmol, 2.2 eq) while maintaining the internal temperature below 5° C. To the reaction mixture was added water (120 mL) and the resulting solution was allowed to stir for 18 hours at 40° C. Toluene (210 mL) was added and the aqueous layer was cut and then discarded. The organic layer was washed sequentially with 2.5 N HCl (255 mL), 5% NaHCO₃ (150 mL) and water (150 mL). The organic phase was concentrated in vacuo to 150 mL and then azeotropically distilled at constant volume (150 mL) with toluene (300 mL) to provide a solution of compounds 1a and 1b (32:68 ratio of 1a:1b), which was used in the next step without further purification.

Compound 1a: ¹H NMR (CDCl₃, 500 MHz): δ 9.99 (s, NH), 7.42 (d, J=8.1 Hz, 1H), 5.9 (d, J=3.7 Hz, 1H), 5.70 (d, J=8.2 Hz, 1H), 5.18 (dd, J=5.6, 3.8 Hz, 1H), 4.24-4.40 (m, 3H), 4.16 (dd, J=6.8, 4.2, 2.8 Hz, 1H), 3.71 (d, J=4.5 Hz, OH), 1.19 (s, 18H); ¹³C NMR (CDCl₃, 125 MHz,): δ 178.25, 177.97, 163.72, 150.21, 140.12, 102.74, 88.53, 81.60, 75.33, 69.09, 63.38, 38.92, 38.81, 27.17, 27.04; HRMS [M+H]⁺ for $C_{19}H_{29}N_2O_8$ calc'd 413.1924; found 413.1928.

Compound 1b: ¹H NMR (CDCl₃, 500 MHz): δ 10.25 (s, NH), 7.49 (d, J=8.2 Hz, 1H), 5.87 (d, J=4.8 Hz, 1H), 5.70 (d, J=8.2 Hz, 1H), 4.93 (t, J=5.2 Hz, 1H), 4.54 (d, J=4.8 Hz, OH), 4.24-4.40 (m, 4H), 1.17 (s, 18H). ¹³C NMR (CDCl₃, 125 MHz,): δ 177.94, 177.92, 163.62, 150.93, 139.29, 102.81, 89.83, 79.97, 73.51, 71.09, 63.07, 38.86, 38.81, 27.15, 27.00; HRMS [M+H]⁺ for $C_{19}H_{29}N_2O_8$ calc'd 413.1924; found 413.1917.

Example 3

Preparation of Compound 2

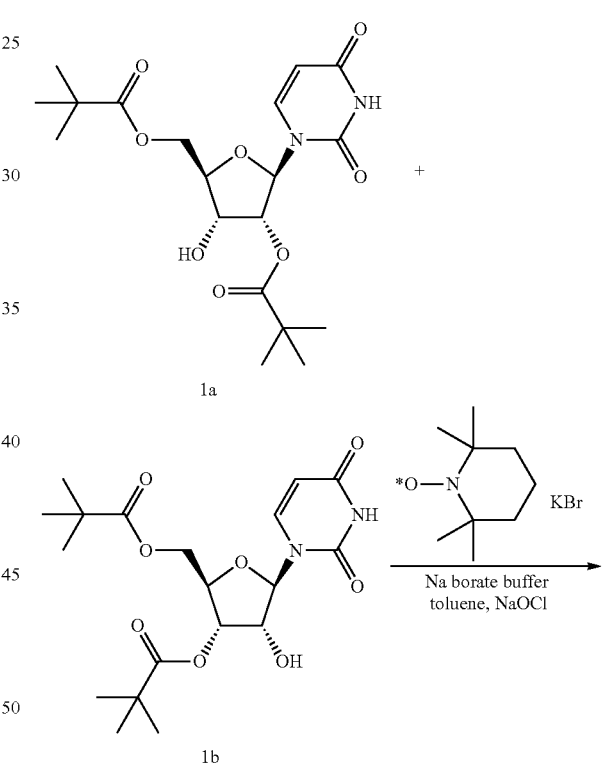

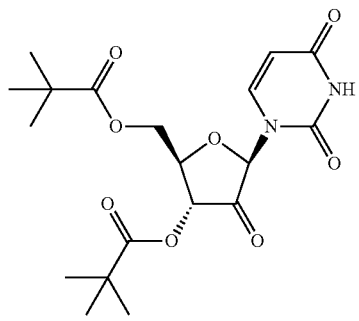

2

To a 500 mL jacketed round bottom flask equipped with overhead stirrer, thermostat and circulating chiller was charged a toluene solution of dipivaloyluridines 1a and 1b (36:64) (14.75 g assayed in total 111 mL toluene, 35.8 mmol), toluene (44 mL) and 3.3 eq 1 M Na borate pH 7.5 buffer (118 mL, 118 mmol, prepared by combining 15.46 g $B(OH)_3$ and 200 mL $H_2O$ (pH 3.3), adjusting pH to 7.5 with ~4.8 mL 10 N NaOH, then diluting with water to a total of 250 mL). The resulting reaction was allowed to stir at 20° C. until the ratio of 1a:1b was approximately 23:77 (as monitored using HPLC assay at 261 nm). To the resulting reaction mixture was then added solid KBr (0.426 g, 3.58 mmol), TEMPO (0.559 g, 3.58 mmol), and 11.7% NaOCl (31.3 mL, 59.0 mmol, added dropwise) over 5 hours while maintaining the internal reaction temperature at 20° C. After the NaOCl addition was complete, the reaction mixture was allowed to stir for an additional 30 minutes, then transferred to a separatory funnel. The reaction vessel was rinsed with DCM (295 mL) and $H_2O$ (74 mL) and the rinses were added to the separatory funnel. The organic layer was collected and the aqueous phase was back-extracted twice with DCM (1×74 mL and 1×15 mL). The combined organic extracts were washed with 5% NaCl solution (148 mL), dried over $Na_2SO_4$, filtered and the filter cake was washed with DCM. The combined filtrate and wash were concentrated in vacuo and the residue obtained was vacuum dried overnight to provide compound 2 as a solid.

Compound 2: $^1$H NMR ($CDCl_3$, 500 MHz): δ 11.71 (s, NH), 7.85 (d, J=8.0 Hz, 1H), 5.76 (s, 1H), 5.72 (d, J=7.9 Hz, 1H), 5.31 (d, J=7.3 Hz, 1H), 4.37 (dt, J=7.3, 5.2 Hz, 1H), 4.31 (dd, J=11.8, 4.6 Hz, 1H), 4.23 (dd, J=11.8, 5.4 Hz, 1H), 1.19 (s, 9H), 1.15 (s, 9H); $^{13}$C NMR ($CDCl_3$, 125 MHz,): δ 201.96, 177.13, 177.04, 163.14, 150.22, 144.69, 102.39, 84.40, 75.93, 70.68, 62.97, 38.31, 38.06, 26.78, 26.54; HRMS $[M+H]^+$ for $C_{19}H_{27}N_2O_8$ calc'd 411.1767; found 411.1765.

Example 4

Alternate Preparation of Compound 2

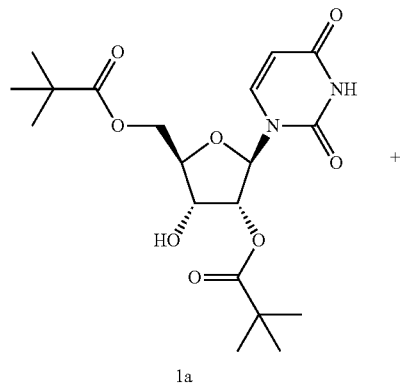

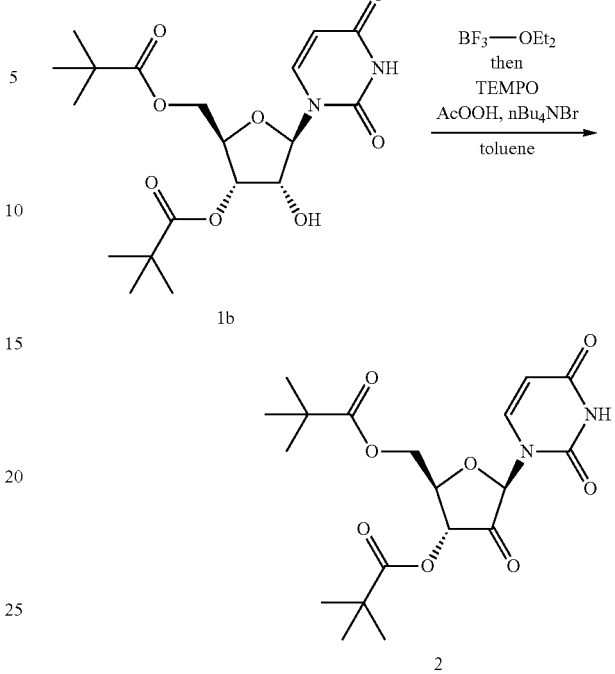

Solution A Preparation:

To a 500 mL jacketed round bottom flask was charged a toluene solution of dipivaloyluridines 1a and 1b (48.1 g, 32:68 ratio of 1a:1b, assayed in a total of 150 mL toluene, 117 mmol). To the mixture was added toluene (180 mL), followed by boron trifluoride diethyletherate (19.2 g, 135 mmol). The reaction mixture was allowed to stir overnight at room temperature and the resultant slurry was washed with water (2×210 mL) to provide a toluene solution of dipivaloyluridines 1a and 1b (Solution A, 1:50 ratio of 1a:1b, assayed in a total 330 mL toluene, 113 mmol).

To a 500 mL jacketed round bottom 3-necked flask equipped with overhead stirrer, thermostat and circulating chiller was charged toluene (92 mL), followed by TEMPO (2.65 g, 17.0 mmol) and tetrabutyl ammonium bromide (3.65 g, 11.3 mmol). The reaction mixture was cooled to 0° C. and to the cooled mixture were simultaneously added both Solution A and peracetic acid (39 wt % in acetic acid, 33.1 g, 166 mmol) through separate necks over 3 hours each while maintaining the internal reaction temperature at 0° C. After the additions were complete, the reaction mixture was allowed to stir for an additional 30 minutes at 0° C., then dioctyl sulfide (17.0 g, 65.7 mmol) was added and the reaction slurry was warmed to room temperature. The product was then isolated by direct crystallization from the reaction mixture, and vacuum dried overnight to provide compound 2 as a solid.

Compound 2: $^1$H NMR ($CDCl_3$, 500 MHz): δ 11.71 (s, NH), 7.85 (d, J=8.0 Hz, 1H), 5.76 (s, 1H), 5.72 (d, J=7.9 Hz, 1H), 5.31 (d, J=7.3 Hz, 1H), 4.37 (dt, J=7.3, 5.2 Hz, 1H), 4.31 (dd, J=11.8, 4.6 Hz, 1H), 4.23 (dd, J=11.8, 5.4 Hz, 1H), 1.19 (s, 9H), 1.15 (s, 9H); $^{13}$C NMR ($CDCl_3$, 125 MHz,): δ 201.96, 177.13, 177.04, 163.14, 150.22, 144.69, 102.39, 84.40, 75.93, 70.68, 62.97, 38.31, 38.06, 26.78, 26.54; HRMS $[M+H]^+$ for $C_{19}H_{27}N_2O_8$ calc'd 411.1767; found 411.1765.

Example 5

Preparation of Compound 3

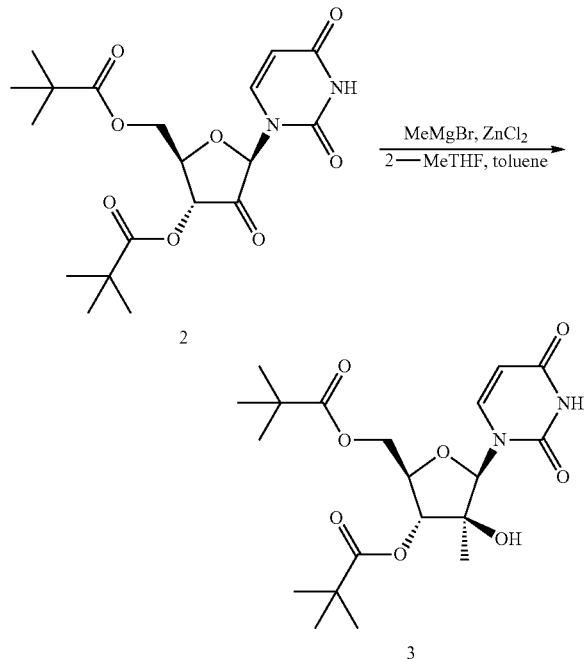

To a dry round bottom flask was charged 2-MeTHF (30 mL, Kf=28 ppm), ZnCl$_2$ and 2-MeTHF (1.9 m solution, 16.0 mL, 30.5 mmol,) and the resulting mixture was cooled to 0° C. under N$_2$ atmosphere. To the cold mixture was slowly added a solution of CH$_3$MgBr in Et$_2$O (3.0 M, 20.3 mL, 60.9 mmol,) while maintaining the internal reaction temperature below 10° C. After the CH$_3$MgBr addition, the resulting slurry was allowed to warm to room temperature and stirred for 1 hour. The slurry was then cooled again to 0° C. and a slurry of compound 2 (5.0 g, 12.18 mmol) in toluene (100 mL, Kf=24 ppm) was slowly added to the first slurry while maintaining the internal reaction temperature below 10° C. The reaction mixture was then allowed to stir at room temperature for 24 hours. The reaction mixture was cooled to 10° C. and quenched with 1N HCl (75 mL) and the resulting mixture was allowed to stir at room temperature for 1 hour. The layers were separated and the aqueous layer was back extracted with toluene (1×25 mL). The combined organic layers were washed with brine (1×25 mL), dried over MgSO$_4$ and filtered and the filter cake rinsed with toluene (2×10 mL) then dried to provide compound 3.

Example 6

Alternate Preparation of Compound 3

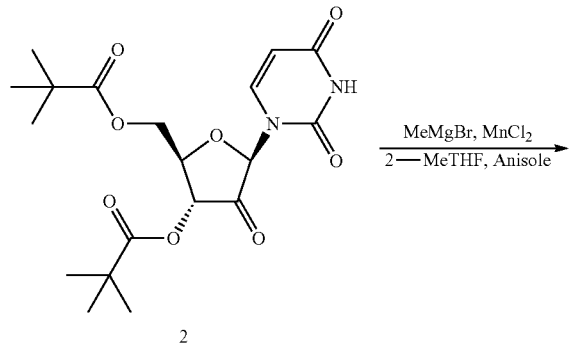

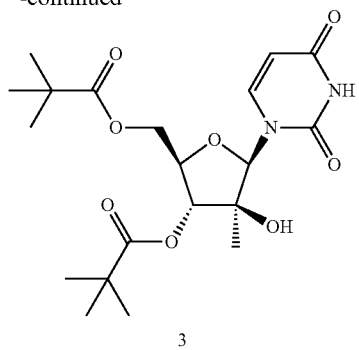

A slurry of anhydrous MnCl$_2$ (2.4 equiv) in dry anisole was wet-milled at room temperature for 5-10 minutes and then a solution of MeMgBr in 2-MeTHF (2.4 equiv) was added and the resulting slurry was allowed to age for 3 hours. To this mixture was added a slurry of 2'-ketouridine in dry 2-MeTHF over 3-6 hours, while maintaining the temperature between −20° C. and 0° C. Once the reaction was complete, the slurry was poured slowly into a pre-cooled solution of 1N HCl and the resulting mixture was agitated and allowed to settle. The organic layer was separated and washed 2× with 15-25 wt % NaCl, filtered and concentrated in vacuo to remove most of the 2-MeTHF. The resulting mixture was used in the next step without further purification.

$^1$H NMR (CDCl$_3$, 500 MHz): δ 9.58 (s, 1H), 7.68 (d, J=8.2 Hz, 1H), 6.04 (s, 1H), 5.64 (dd, J=8.2, 1.6 Hz, 1H), 4.90 (d, J=3.2 Hz, 1H), 4.59 (dd, J=11.9, 7.0 Hz, 1H), 4.33 (dd, J=11.9, 4.0, Hz, 1H), 4.10 (ddd, J=7.1, 4.0, 3.2, Hz, 1H), 1.42 (s, 3H), 1.25 (s, 9H), 1.24 (s, 9H). $^{13}$C NMR (CDCl$_3$, 125 MHz,): δ 178.44, 177.75, 164.22, 150.93, 142.81, 101.44, 89.50, 81.16, 79.77, 79.22, 63.51, 39.11, 39.04, 27.37, 27.25, 19.63. HRMS [M+H]$^+$ for C$_{20}$H$_{31}$N$_2$O$_8$ calc'd 427.2080; found 427.2092.

Example 7

Preparation of Compound 4

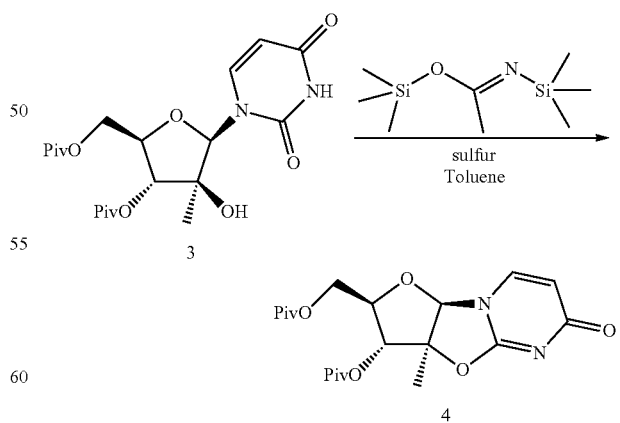

Compound 3 (426 mg, 1.00 mmol) and elemental sulfur (10.6 mg, 0.33 mmol) were added to a 20 mL septum capped vial and the vial was purged with nitrogen. To the vial was added bis(trimethylsilyl)acetamide (733 µl, 3.00 mmol) and the resulting reaction was heated to 90° C. and allowed to stir at this temperature for 2.5 hours. Heptane (5 mL) then was added over a 20 minute period and the resulting solution was cooled to 22° C., then filtered. The collected filter cake was washed with 1:1 toluene-heptane (10 mL), then dried to provide compound 4, which was used without further purification.

¹H NMR (CDCl₃, 500 MHz) δ 7.40 (d, J=7.5 Hz, 1H), 6.11 (d, J=7.5 Hz, 1H), 5.86 (s, 1H), 5.40 (d, J=3.3 Hz, 1H), 4.32 (m, 1H), 4.12 (dd, J=12.1, 6.6 Hz, 1H), 4.06 (dd, J=12.1, 5.6 Hz, 1H), 1.72 (s, 3H), 1.27 (s, 9H), 1.17 (s, 9H). ¹³C NMR (CDCl₃, 125 MHz) δ 177.58, 176.55, 171.60, 158.95, 134.90, 110.67, 94.40, 94.24, 84.28, 76.62 61.94, 38.88, 38.78, 27.02, 27.00, 17.75.

Example 8

Preparation of Compound 5

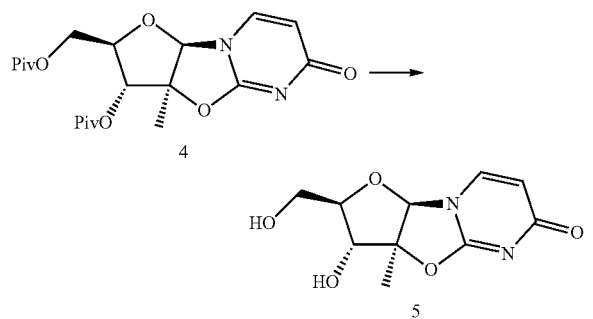

To a solution of compound 4 (408 mg, 1 mmol) in methanol (4901 μl) was added potassium carbonate (27.6 mg, 0.200 mmol). The resulting reaction was heated to 50° C. and allowed to stir at this temperature for 3 hours, then the reaction mixture was cooled to 20° C. over a 1 hour period. The resulting slurry was filtered and the filter cake was washed with methanol (4901 μl) and dried under a stream of nitrogen to provide compound 5.

Example 9

Alternate Preparation of Compound 5

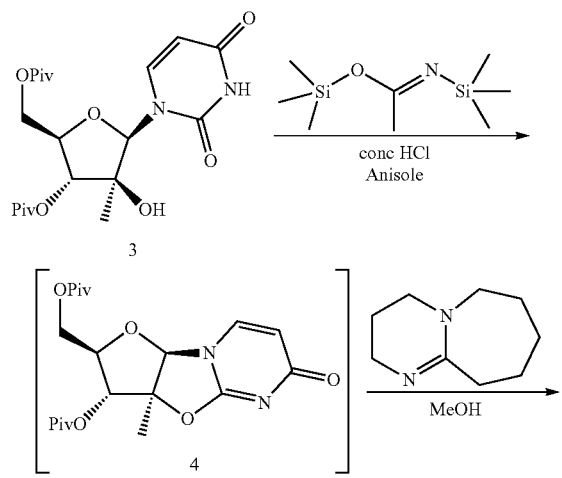

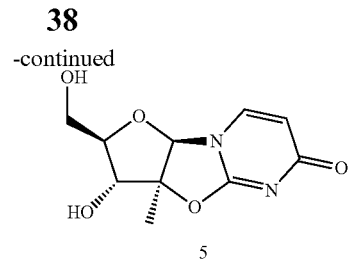

Compound 3 (9.38 g, 22.0 mmol) as a 15.9 wt % solution in anisole and 37 wt % aqueous HCl (18 μl, 0.22 mmol) were added to a 300 mL flask. The mixture was purged with nitrogen and heated to 70° C. To the mixture was added bis(trimethylsilyl)acetamide (13.4 g 66.0 mmol) dropwise over 1 hour while maintaining the reaction temperature at 70° C. and allowed to stir at this temperature for 7 hours. This slurry mixture (containing compound 4) was then cooled to 60° C. Methanol (37.5 mL) and 1,8-Diazabicyclo [5.4.0]undec-7-ene (DBU, 2.51 g, 16.5 mmol) were added and the resulting reaction was allowed to stir at 60° C. for 22 hours, then the reaction mixture was cooled to 10° C. over a 1 hour period and allowed to stir at this temperature for an additional 1 hour. The resulting slurry was filtered and the filter cake was washed with 2:1 by volume methanol-anisole (10 mL) then with ethanol (30 mL) and dried under a stream of nitrogen to provide compound 5.

Example 10

Preparation of Compound 6

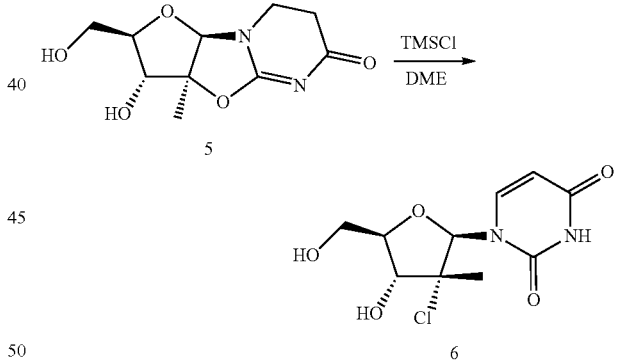

A 40 cc septum cap vial with stir bar in a metal heating block was charged with compound 5 (2 g, 8.33 mmol), 1,2-dimethoxyethane (20.00 mL), DMF (1.289 mL, 16.65 mmol) and TMS-Cl (3.83 mL, 30.0 mmol). The resulting slurry was heated to 90° C. and allowed to stir at this temperature for 36 hours. The reaction mixture was then filtered into a second 40 cc vial. Water (0.150 mL, 8.33 mmol) was added and the resulting solution was allowed to stir for 30 minutes at room temperature. The reaction mixture was then solvent switched to a final quantity of MEK (6.00 mL) by evaporation down to 6 mL volume and flushed with MEK (30 mL). The resulting slurry was filtered on a sintered glass funnel and the filter cake was washed with MEK (6.00 mL) and dried to provide compound 6 as a solid.

Example 11

Alternate Preparation of Compound 6

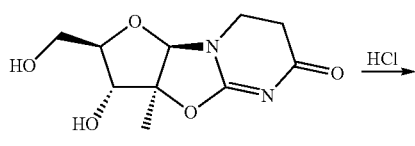

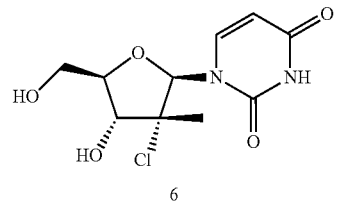

A mixture of compound 5 (0.096 g, 0.25 mmol), DME (1 mL) and 4 M aqueous HCl (0.188 mL, 0.750 mmol) in 1,3-dioxane was heated to 110° C. and allowed to stir at this temperature for 16 hours. The reaction mixture was then solvent switched to a final quantity of MEK (5.00 mL) by evaporation down to 5 mL volume and flushed with MEK (20 mL). The resulting slurry was filtered through a sintered glass funnel and the filter cake was washed with MEK (5.00 mL) and dried to provide compound 6 as a solid.

Example 12

Alternate Preparation of Compound 6

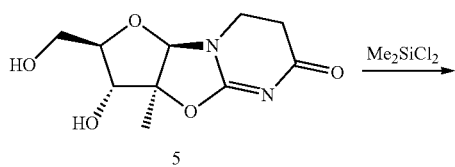

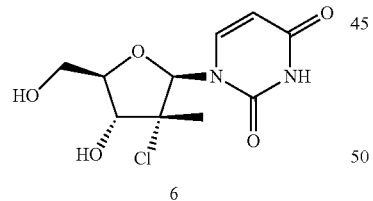

A mixture of compound 5 (40.0 g, 167 mmol), DME (400 mL), DMF (6.45 mL, 83 mmol) and Me$_2$SiCl$_2$ (60.8 mL, 500 mmol) was heated to 70° C. and allowed to age for 4-8 hours. The reaction mixture was then cooled to room temperature, concentrated in vacuo to 140 mL (3.5× total volume), then quenched using water (80 mL). The biphasic mixture was washed with n-heptane (40 mL) and the resulting upper layer was discarded. The bulk solution was then charged with FeCl$_3$.(H$_2$O)$_6$ (11.22 g, 83.5 mmol) followed by tetramethyldisiloxane (7.38 mL, 83.5 mmol) and allowed to age 2-4 hours at 25° C. 2-MeTHF (320 mL), water (120 mL), and Na$_2$SO$_4$ (42 g) were then added, and the reaction mixture was heated to 30-35° C. and thoroughly mixed. Agitation was halted, and the lower aqueous layer was collected. 17 wt % Na$_2$SO$_4$ (200 mL) was added and thoroughly mixed. Agitation was halted and the lower aqueous layer was collected and diluted with MIBK (140.1 mL). The mixture was then solvent switched to pure MIBK and the resulting solids were collected by filtration, dried over nitrogen and used without further purification.

Example 13

Preparation of Compound 7

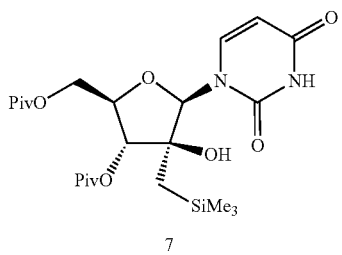

A solution of compound 2 (6.25 g, 1 equiv) in cyclopentyl methyl ether (CPME) (30 mL) was cooled to 0° C., and to the cooled solution was added a 1 M solution of TMSCH$_2$MgCl (42.6 mL, 2.5 equiv) in diethyl ether over a 15-30 minute period. The resulting reaction was allowed to stir overnight at room temperature, then 2N HCl was then added. The result in reaction was allowed to stir for 10 minutes at room temperature, the organic layer was separated and washed with brine, dried over MgSO$_4$ and filtered to provide compound 7 as foamy solid.

Example 14

Preparation of Compounds 8 and 9

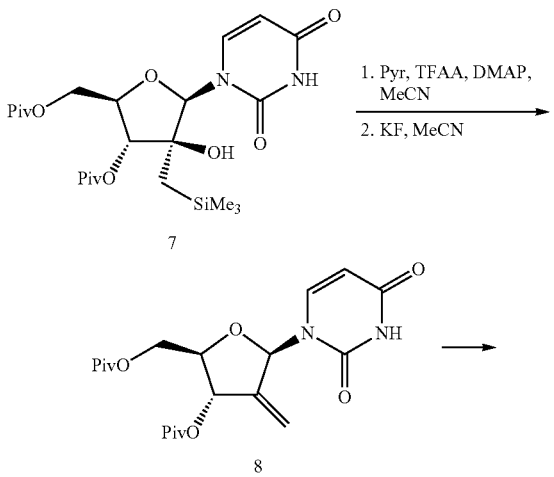

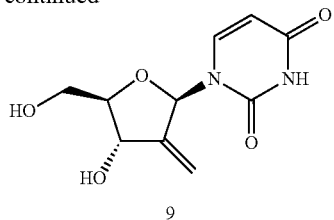

9

To a solution of compound 7 (1 g, 1 equiv) in dry acetonitrile was added trifluoroacetic anhydride (0.75 mL, 3 equiv), pyridine (0.48 mL, 3 equiv) and DMAP (49 mg, 0.2 equiv) and the resulting reaction was allowed to stir at room temperature for 15 hours. Potassium fluoride (0.45 g, 3.5 equiv) was then added and the resulting reaction was heated to 70° C. and allowed to stir at this temperature for 24 hours. MTBE was then added, followed by H$_2$O. The organic layer was separated and washed with another portion of water, followed an aqueous solution containing 2 equiv of K$_2$CO$_3$ and brine. The final organic layer was concentrated in vacuo to provide crude olefin 8 (720 mg) 88% yield as a solid. The crude product was dissolved in a mixture of MeOH and THF, treated with K$_2$CO$_3$ (2-3 equiv) and allowed to age for 15 hours at 40° C. The reaction was then concentrated in vacuo and solvent switched to 2-MeTHF (6 mL) and treated with 4M HCl (2 equiv) in dioxane. The resulting slurry was concentrated in vacuo to half of its volume to provide compound 9 as a solid.

Example 15

Alternate Preparation of Compounds 8 and 9

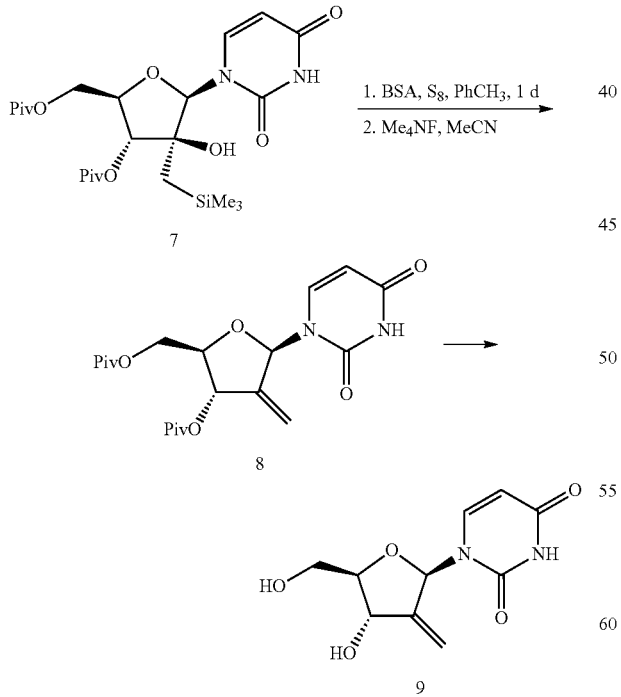

Step 1—Synthesis of Compound 8
A mixture of compound 7 (49.9 mg, 0.1 mmol), toluene (598 μl) and elemental sulfur (1.058 mg, 0.033 mmol) was purged with nitrogen. To the resulting mixture was added N,O-bis(trimethylsilyl)acetamide (73.4 μl, 0.300 mmol) and the resulting reaction was heated to 80° C. and allowed to stir at this temperature for 60 hours. Heptane (1 mL) was then added to the mixture at 70° C. over a 20 minute period and the resulting reaction was allowed to cool to room temperature over 30 minutes. Acetonitrile (1 mL) was added to the reaction mixture, followed by TBAF (5 mg), and the resulting reaction was allowed to stir for 5 minutes. Methanol was then added followed by K$_2$CO$_3$ and the resulting reaction was heated to 45° C. and allowed to stir at this temperature for 12 hours. The product was then isolated by direct crystallization from the reaction mixture to provide compound 8.

Step 2—General Procedure for Hydrolysis of Compound 8
To a solution of compound 8 (0.3 gram, 1 equiv) in THF:MeOH (2 mL) at room temperature was added solid K$_2$CO$_3$ (0.2 gram, 1 equiv) and the resulting slurry was allowed to age at 35° C. for 15 hours. Another equivalent of K$_2$CO$_3$ (0.2 gram) was added and the resulting slurry was allowed to age at 40° C. for 15 hours, at which point it was concentrated in vacuo and solvent switched to 2-MeTHF (6 mL), then treated with 4M HCl (2 equiv) in dioxane. The resulting slurry was concentrated in vacuo to half of its volume to provide compound 9 as a solid.

Example 16

Alternate Preparation of Compounds 8 and 9

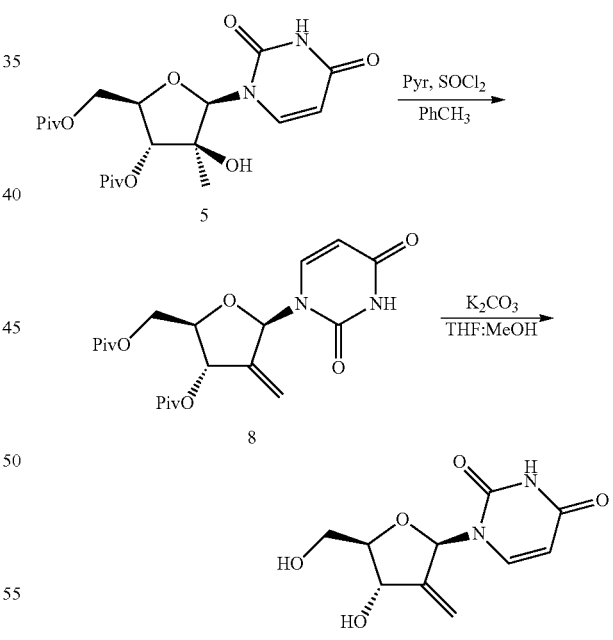

Step 1—Synthesis of Compound 8
To a mixture of compound 5 (107 mg, 0.25 mmol) and pyridine (60.7 μl, 0.750 mmol) in toluene (2132 μl) was added thionyl chloride (27.4 μl, 0.375 mmol). The reaction mixture was heated to 70° C. and allowed to stir at this temperature for 16 hours. The reaction mixture was diluted with EtOAc (1 mL) and washed with water (2 mL). The organic phase was dried over MgSO$_4$ and filtered through a plug of silica in Pasteur pipet. The filtrate was concentrated in vacuo, and the resulting residue was suspended in warm MTBE (0.5 cc) then cooled to room temperature, and hexane (0.5 mL) was added over a 20 minute period. The resulting solution was cooled to −20° C. and allowed to stir at this temperature for 1 hour. The reaction mixture was then filtered and concentrated in vacuo to provide compound 8 (50 mg, 0.122 mmol, 49.0% yield).

Step 2—General Procedure for Hydrolysis of Compound 8 See Example 15, Step 2.

Example 17

Alternate Preparation of Compound 6

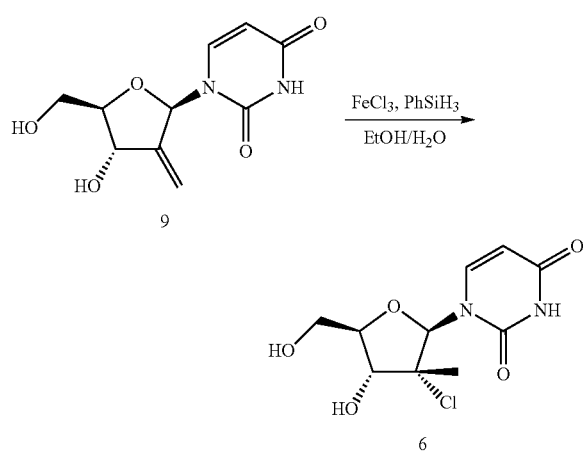

To a room temperature solution of compound 9 (1 g, 1 equiv) in water (80 mL) was added iron (III) chloride (2 g, 3 equiv). Phenylsilane (3.2 mL, 6 equiv) was then added over a 1 hour period and the reaction was allowed to stir at room temperature for 48 hours. The reaction mixture was then diluted with 1:1 MTBE:hexanes (40 mL), stirred rigorously and allowed to settle. The aqueous layer was separated and assayed to confirm the presence of product 6. The aqueous layer was then treated with 3 equiv of EDTA-disodium salt and saturated with NaCl and product was extracted with 2-MeTHF (3×50 mL). The combined organic extracts were washed with brine and concentrated in vacuo to provide compound 6 as a solid.

Example 18

Alternate Preparation of Compound 11

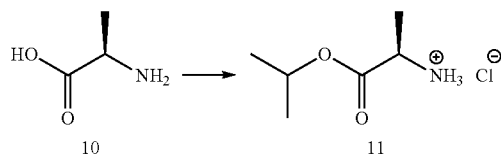

A 1 L flask was charged with D-Alanine (10, 50 g, 561 mmol) and iPrOH (432 mL). To the resulting solution was added TMS-Cl (108 mL, 842 mmol, 1.5 eq) and the reaction was allowed to stir at 70° C. for 19 hours. The mixture was then concentrated in vacuo at 35° C. to 189 g total weight, then diluted with iPrOH (350 mL). The mixture was concentrated in vacuo to 118 g weight, then diluted with iPrOH (390 mL). TMS-Cl (36 mL, 281 mmol, 0.50 equiv) was added and the resulting reaction was allowed to stir at 70° C. for 20 hours. The reaction mixture was then concentrated in vacuo to 140 g weight, then concentrated in vacuo with IPAC (four portions of 250 mL) to 124 g final weight. The resulting residue was diluted with 250 mL IPAC to provide a mixture containing compound 2. A portion of the mixture, compound 2, was used without further purification.

Example 19

Alternate Preparation of Compound 12

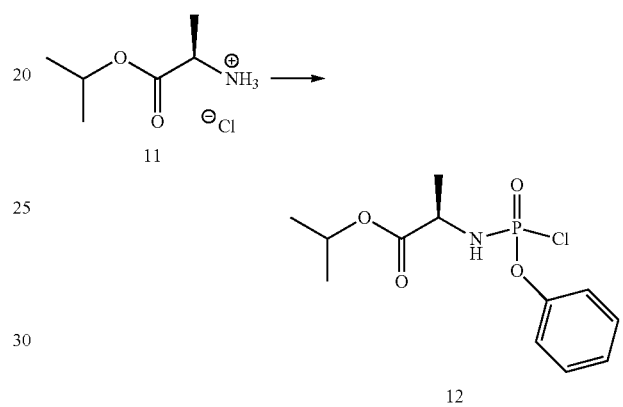

A 500 mL jacketed round bottom flask with mechanical stirrer and nitrogen inlet was charged with a mixture of compound 11 (58 mmol, 1.2 equiv) in IPAC (100 mL). The mixture was cooled to 15° C., then phenyl dichlorophosphate (7.2 mL, 48 mmol) was added while keeping the reaction temperature below −9° C. Triethylamine (15.5 mL, 111 mmol, 2.3 equiv) was then added over a two hour period while maintaining the reaction temperature at about −15° C. The reaction mixture was allowed to stir at −15° C. for 20 hours, then was warmed to room temperature. The resulting slurry was filtered in a dry, inert atmosphere and the filter cake was washed twice with IPAC (40 mL). The combined filtrate and washings were concentrated in vacuo to provide compound 12 as an oil (50 wt %) that was used without further purification.

Example 20

Preparation of Compound A

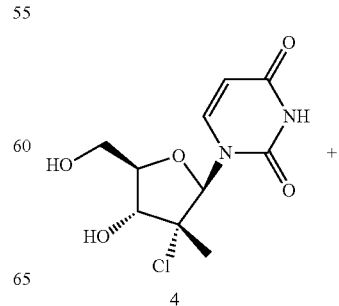

45

-continued

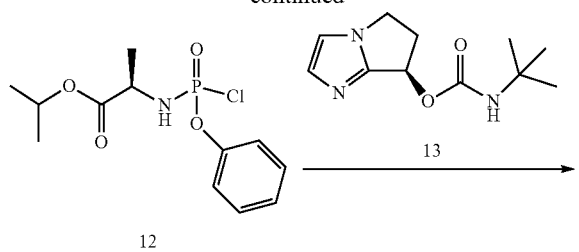

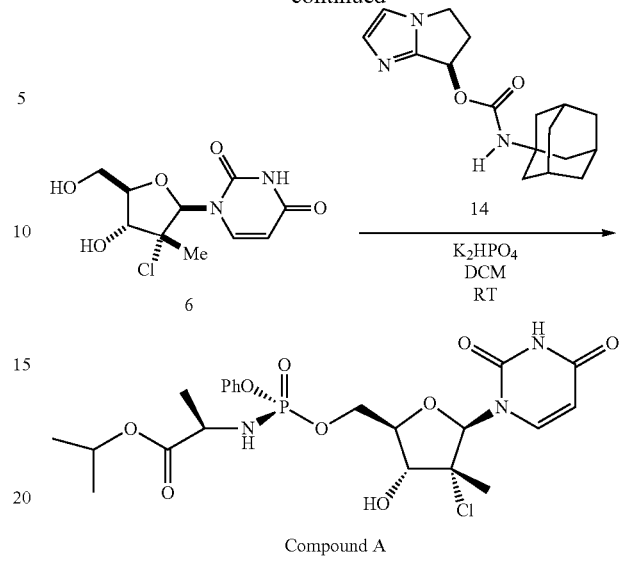

A 3-neck 100 mL jacketed round bottom flask with nitrogen inlet and mechanical stirrer was charged with compound 4 (3.0 g, 10.8 mmol), compound 13 (0.484 g, 2.17 mmol, 0.20 equiv), 2-butanone (21 mL), and 2,6-lutidine (2.53 mL, 21.7 mmol, 2.0 equiv). The resulting slurry was cooled to −15° C., then a solution of compound 12 (7.96 g, 13.0 mmol) in 2-butanone (3 mL) was added over 14 hours. The reaction mixture was allowed to stir at −15° C. for an additional 25 hours and then warmed to 20° C. n-Heptane (16 mL) was added with stirring over a 1 hour period then the mixture was allowed to stir at 25° C. for 3 hours, then filtered through a fritted funnel. The filter cake was slurry-washed with a 3:2 mixture of 2-butanone and n-heptane (10 mL and then 15 mL), then dried by pulling nitrogen stream through the fritted funnel. The filter cake was slurried in a 10:1 mixture of water and 2-butanone (21 mL) and then filtered. This slurrying and filtration sequence was repeated two more times. The resulting filter cake was dried with nitrogen stream through the fritted funnel to provide compound 6.

Example 21

Alternate Preparation of Compound A

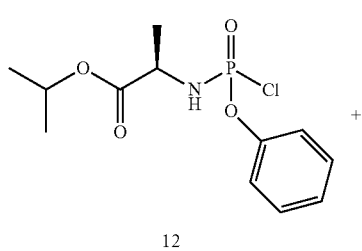

46

-continued

Compound 6 (0.072 mmol, 1 equiv), K$_2$HPO$_4$ (63.0 mg, 0.361 mmol) and compound 14 (5.45 mg, 0.018 mmol) were added to a 1 dram vial with 4A mol sieves (40 mg). To the resulting mixture was added DCM (800 µl), then the resulting reaction was allowed to stir for 5 minutes. To the reaction mixture was then added compound 14 (28.7 mg, 0.094 mmol, 1.3 equiv) and the resulting reaction was allowed to stir for about 15 hours at room temperature to provide Compound A.

Example 22

Preparation of Compound 15

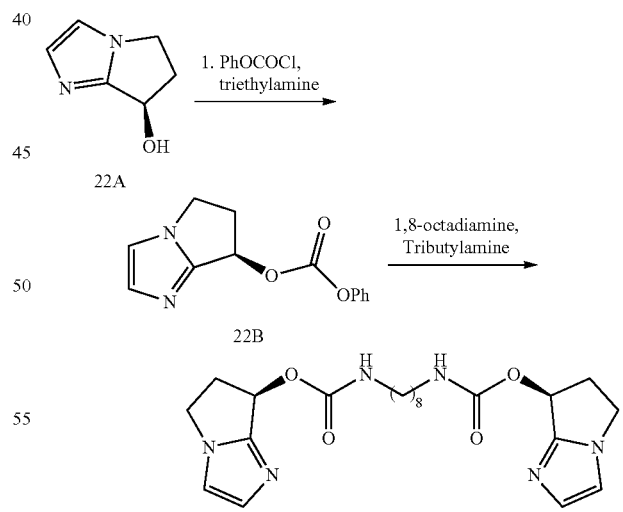

Compound 22A (1 g, 8.06 mmol, which is commercially available or can be made using the method described in Zhang et al., Advanced Synthesis & Catalysis (2014), 356 (14-15), 3164-3170) was dissolved in THF (5 mL). To the resulting solution was added triethylamine (1.75 mL, 12.08 mmol), followed by phenylchloroformate (1.119 mL, 8.86 mmol, added via syringe over a 5 minute period). The resulting reaction was allowed to stir for 2 hours, then filtered to remove precipitate and the filtrate (containing 22B as its triethylamine salt) was treated with tributylamine (2.3 mL, 9.67 mmol) and 1,8-diaminooctane (0.581 g, 4.03 mmol), and the resulting reaction was allowed to stir overnight. The reaction mixture was then filtered to provide a solid, which was then triturated with 5 mL THF to provide compound 15.

Example 23

Alternate Preparation of Compound A

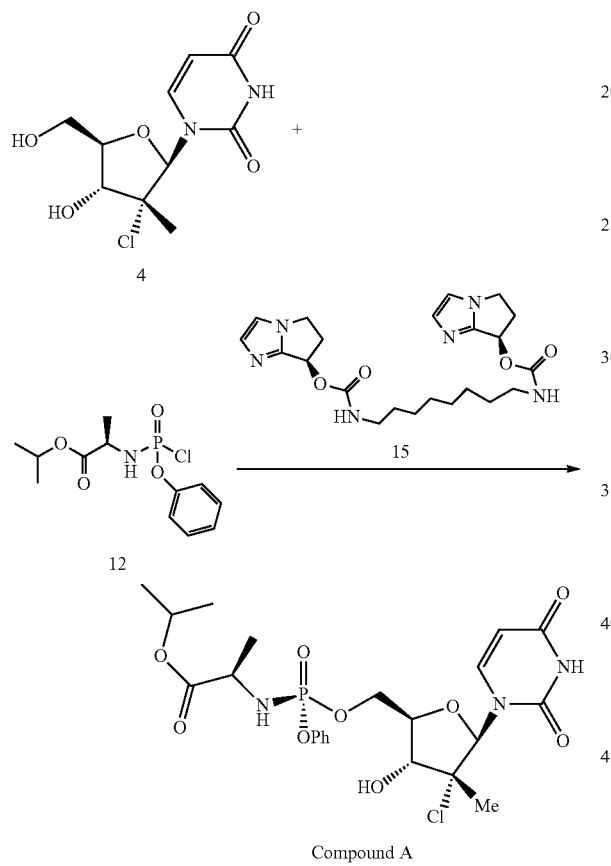

A 100 mL reactor with nitrogen inlet and mechanical stirrer was charged with compound 4 (7.00 g, 25.3 mmol), compound 15 (0.225 g, 0.506 mmol, 0.020 equiv), 1,3-dioxolane (42 mL), and 2,6-lutidine (4.42 mL, 38.0 mmol, 1.5 equiv). The mixture was cooled to −10° C. and a 33 wt % solution of compound 12 in isopropyl acetate (29 mL, 30 mmol) was added over 1 hour. The reaction mixture was allowed to stir at −10° C. for additional 40 hours, then isopropyl acetate (28 mL) was added, and the resulting mixture was warmed to 0° C. A 10 wt % aqueous NaHSO$_4$ solution was added (14 mL), and the mixture was allowed to stir at 30° C. for 30 minutes, then the layers were separated. To the organic layer was added an aqueous solution containing 5 wt % NaHCO$_3$ and 5 wt % Na$_2$SO$_4$ (21 mL). The mixture was allowed to stir at 50° C. for 6 h. The layers were separated. To the organic layer was added 10 wt % aqueous NaCl solution (21 mL). The mixture was allowed to stir at 50° C. for 30 min. The organic layer was separated, combined with isopropyl acetate (5 mL) and concentrated in vacuo to half volume at 20000 pa in a 50° C. bath. The resulting solution was solvent-switched with isopropanol (4×35 mL) to 60 g weight. The mixture was seeded with 100 mg of compound A at 60° C. The resulting slurry was allowed to stir at 55° C. for 30 minutes, then n-Heptane (35 mL) was added over 1 hour at 55° C. The resulting slurry was allowed to stir for an additional 1 hour at 55° C., then cooled to room temperature and filtered. The filter cake was washed with a 1:1 mixture of isopropanol and n-heptane (3×14 mL), followed by n-heptane (14 mL), then dried under nitrogen to provide Compound A.

Example 24

Preparation of Compound 16

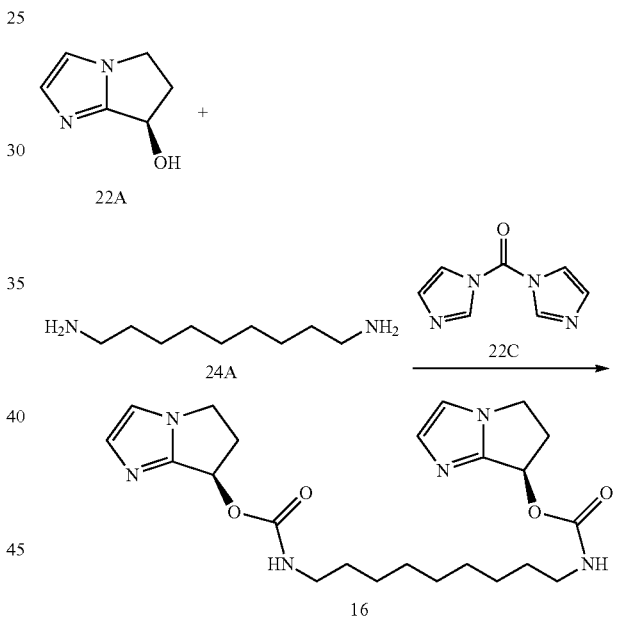

A solution of compound 24A (0.70 g, 4.42 mmol) in THF (4.3 mL) was added to a suspension of compound 22C (1.58 g, 9.7 mmol) in THF (7 mL) while cooling the reaction mixture in an ice bath. The resulting solution was allowed to stir at room temperature for 1.5 hours, then compound 22A (1.10 g, 8.8 mmol) was added. To the resulting solution was added NaH (60% dispersion in oil, 0.35 g, 8.8 mmol) in portions while cooling the reaction mixture in an ice bath. The reaction mixture was then concentrated in vacuo to half volume under nitrogen and quenched with 15 wt % aqueous KH$_2$PO$_4$ solution (8 mL). Water (20 mL) and dichloromethane (50 mL) were added and the layers were separated. The organic phase was washed with water (2×30 mL), then concentrated in vacuo and the residue obtained was purified using flash chromatography on silica gel (eluting with a mixture of (0.02M NH$_3$ in dichloromethane and 0.02M NH$_3$ in MeOH from 100:0 to 85:15) to provide compound 16.

Example 25

Preparation of Compound 17

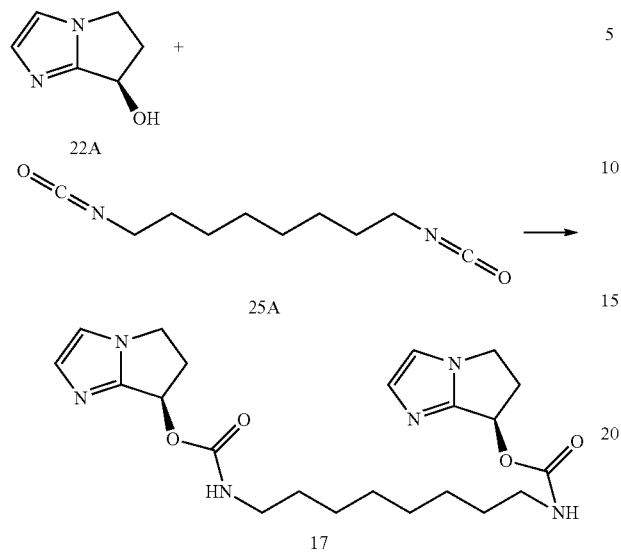

A mixture of compound 22A (1.00 g, 8.1 mmol), 1,8-diazabicyclo[5.4.0]undec-7-ene (0.12 mL, 0.81 mmol) and N,N-dimethylacetamide (3.0 mL) was cooled in an ice bath. Compound 25A (0.71 mL, 3.62 mmol) was added over 30 minutes while cooling the reaction mixture in an ice bath. The reaction was allowed to stir at room temperature for 3 days, then combined with water (9 mL). The resulting slurry was allowed to stir at room temperature and then filtered and the filter cake was washed with water (3×5 mL) and dried. The crude product was purified using flash chromatography on silica gel (eluting with a mixture of dichloromethane and MeOH from 100:0 to 80:20) and the column fractions containing product were solvent switched with isopropyl acetate to 5 mL volume. The resulting slurry was filtered and the filter cake was dried to provide the compound 17. $^1$H NMR (CDCl$_3$, 500 MHz) δ 7.17 (s, 2H), 6.94 (s, 2H), 5.89 (dd, J=7.1, 2.3 Hz, 2H), 5.00 (br s, 1.8H), 4.65 (br s, 0.2H), 4.18-4.10 (m, 2H), 4.00-3.93 (m, 2H), 3.24-3.00 (m, 6H), 2.63-2.57 (m, 2H), 1.53-1.35 (br m, 4H), 1.35-1.20 (br m, 8H). $^{13}$C NMR (CDCl$_3$, 125 MHz) δ 155.67, 151.53, 134.75, 115.37, 67.62, 42.91, 41.01, 35.33, 29.77, 29.02, 26.54.

While the foregoing specification teaches the principles of the present invention, with examples provided for the purpose of illustration, the practice of the invention encompasses all of the usual variations, adaptations and/or modifications that come within the scope of the following claims. All publications, patents and patent applications cited herein are incorporated by reference in their entirety into the disclosure.

What is claimed is:

1. A compound having the formula:

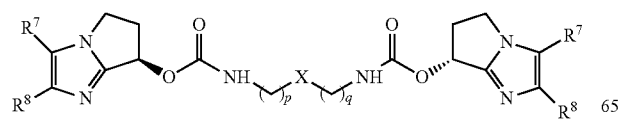

(iib)

X is selected from C$_1$-C$_6$ alkylene, C$_6$-C$_{10}$ arylene, C$_4$-C$_{10}$ cycloalkylene, 5 or 6-membered monocyclic heteroarylene and 9 or 10-membered bicyclic heteroarylene, wherein said C$_6$-C$_{10}$ arylene group, said C$_4$-C$_{10}$ cycloalkylene group, said 5 or 6-membered monocyclic heteroarylene group and said 9 or 10-membered bicyclic heteroarylene group can be optionally substituted with one or more R$^5$ groups;

each occurrence of R$^5$ is independently selected from —C$_1$-C$_6$ alkyl, halo, —OR$^6$, —C(O)R$^6$, —CO$_2$R$^6$, —SR$^6$, —C$_1$-C$_6$ hydroxyalkyl, —C$_1$-C$_6$ haloalkyl, —N(R$^6$)$_2$, —S(O)R$^6$, —S(O)$_2$R$^6$, —CN and —NO$_2$;

each occurrence of R$^6$ is independently selected from H, C$_1$-C$_6$ alkyl, C$_1$-C$_6$ haloalkyl, C$_1$-C$_6$ hydroxyalkyl, —(C$_1$-C$_3$ alkylene)$_m$-(C$_3$-C$_7$ cycloalkyl), —(C$_1$-C$_3$ alkylene)$_m$-(C$_6$-C$_{10}$ aryl), —(C$_1$-C$_3$ alkylene)$_m$-(4 to 7-membered heterocycloalkyl), —(C$_1$-C$_3$ alkylene)$_m$-(5- or 6-membered monocyclic heteroaryl) and —(C$_1$-C$_3$ alkylene)$_m$-(9- or 10-membered bicyclic heteroaryl);

each occurrence of R$^7$ is independently selected from H, C$_1$-C$_6$ alkyl, phenyl, C$_3$-C$_7$ cycloalkyl, 4 to 7-membered monocyclic heterocycloalkyl and 5- or 6-membered monocyclic heteroaryl;

each occurrence of R$^8$ is independently selected from H, C$_1$-C$_6$ alkyl, phenyl, C$_3$-C$_7$ cycloalkyl, 4 to 7-membered monocyclic heterocycloalkyl and 5- or 6-membered monocyclic heteroaryl;

each occurrence of m is independently 0 or 1;

p is 2, 3, 4 or 5; and q is 2, 3, 4 or 5.

2. The compound of claim 1, having the structure:

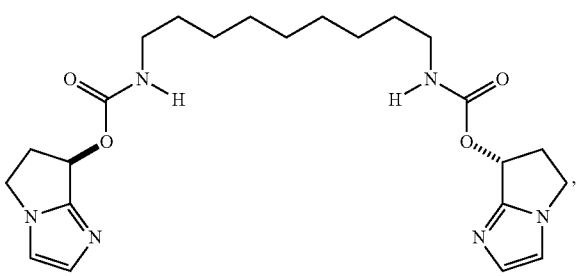

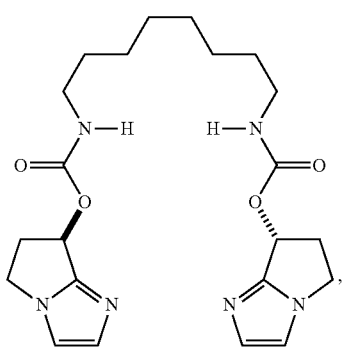

51
-continued
52
-continued
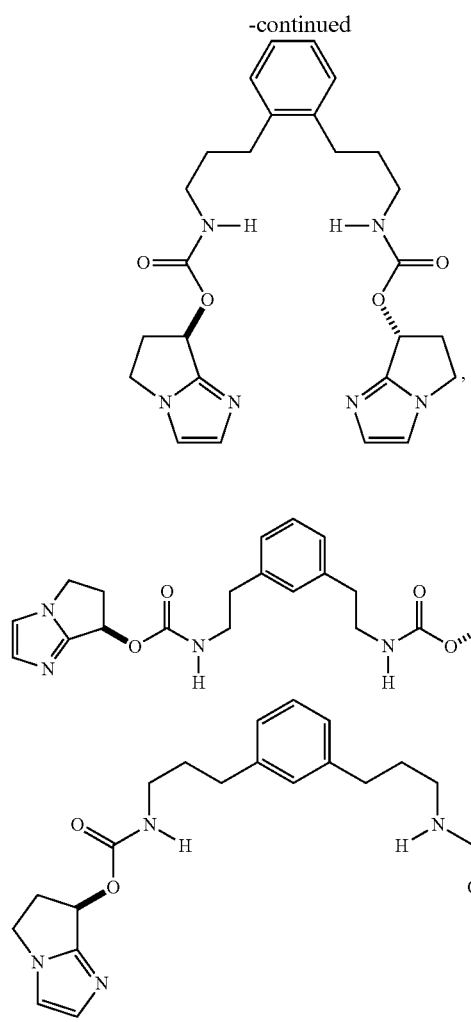
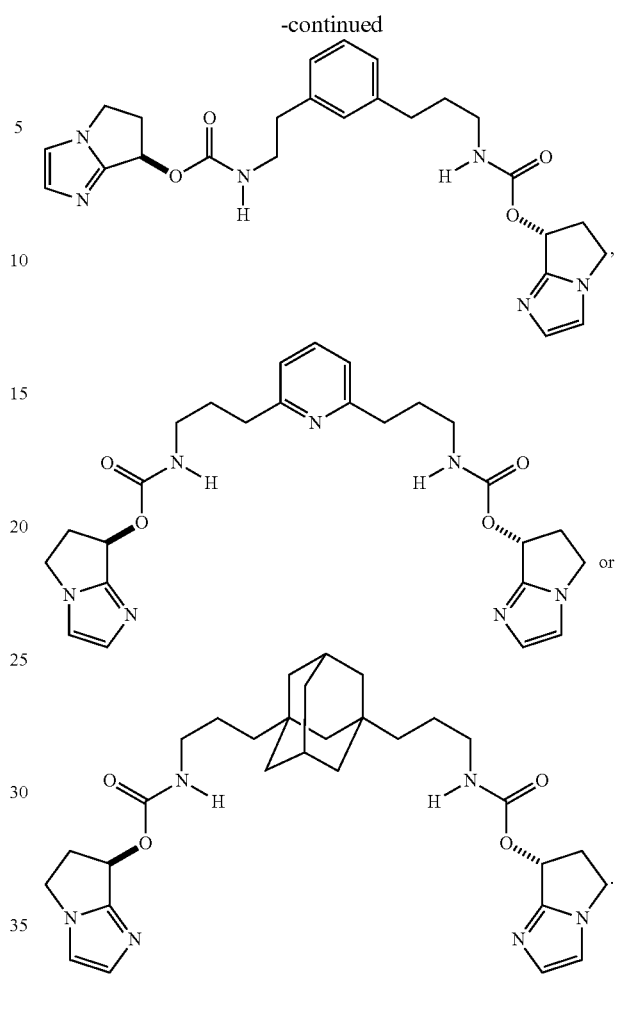
or
* * * * *